US011466063B2

(12) United States Patent
Cochran et al.

(10) Patent No.: US 11,466,063 B2
(45) Date of Patent: *Oct. 11, 2022

(54) CONJUGATED KNOTTIN MINI-PROTEINS CONTAINING NON-NATURAL AMINO ACIDS

(71) Applicant: The Board of Trustees of the Leland Stanford Junior University, Stanford, CA (US)

(72) Inventors: Jennifer R. Cochran, Stanford, CA (US); Jun Woo Kim, Mountain View, CA (US); Frank V. Cochran, Stanford, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/565,243

(22) Filed: Sep. 9, 2019

(65) Prior Publication Data

US 2020/0239531 A1  Jul. 30, 2020

Related U.S. Application Data

(60) Continuation of application No. 15/418,545, filed on Jan. 27, 2017, now Pat. No. 10,407,477, which is a division of application No. 14/435,711, filed as application No. PCT/US2013/065610 on Oct. 18, 2013, now Pat. No. 9,587,001.

(60) Provisional application No. 61/716,363, filed on Oct. 19, 2012.

(51) Int. Cl.
| | |
|---|---|
| *A61K 38/00* | (2006.01) |
| *A61K 47/64* | (2017.01) |
| *A61P 35/00* | (2006.01) |
| *C07K 14/47* | (2006.01) |
| *C07K 14/81* | (2006.01) |

(52) U.S. Cl.
CPC .......... *C07K 14/4702* (2013.01); *A61K 47/64* (2017.08); *C07K 14/811* (2013.01); *A61K 38/00* (2013.01); *C07K 2319/00* (2013.01); *C07K 2319/33* (2013.01)

(58) Field of Classification Search
CPC ......... A61K 38/00; A61K 47/64; A61P 35/00; C07K 14/4702; C07K 14/811; C07K 2319/00; C07K 2319/33; C07K 14/47; C07K 14/81
USPC .......................................... 530/324; 514/12
See application file for complete search history.

(56) References Cited

U.S. PATENT DOCUMENTS

| | | | |
|---|---|---|---|
| 5,518,888 | A | 5/1996 | Waldman |
| 5,766,591 | A | 6/1998 | Brooks et al. |
| 5,827,821 | A | 10/1998 | Pierschbacher et al. |
| 5,916,875 | A | 6/1999 | Ruoslahti et al. |
| 5,981,478 | A | 11/1999 | Ruoslahti et al. |
| 8,361,933 | B2 | 1/2013 | Daugherty et al. |
| 8,394,924 | B2 | 3/2013 | Wittrup et al. |
| 8,536,301 | B2 | 9/2013 | Cochran et al. |
| 8,648,176 | B2 | 2/2014 | Davis Orcutt et al. |
| 8,778,888 | B2 | 7/2014 | Cochran et al. |
| 2009/0257952 | A1* | 10/2009 | Cochran ................ A61K 38/06 424/1.69 |
| 2010/0267610 | A1 | 10/2010 | Blind et al. |
| 2011/0136740 | A1 | 6/2011 | Cochran et al. |
| 2014/0010757 | A1 | 1/2014 | Cochran et al. |
| 2014/0073518 | A1 | 3/2014 | Cochran et al. |
| 2014/0079770 | A1 | 3/2014 | Kusumoto et al. |
| 2014/0235476 | A1 | 8/2014 | La Porte et al. |

FOREIGN PATENT DOCUMENTS

| | | | | |
|---|---|---|---|---|
| WO | WO-2007097934 A2 * | 8/2007 | ......... | A61K 47/6849 |
| WO | WO 2012064658 | 5/2012 | | |
| WO | WO 2012073045 | 6/2012 | | |

OTHER PUBLICATIONS

Conjugation Services from www.dalton.com, pp. 1-2. Feb. 26, 2011. (Year: 2011).*
Thonon et al., "New Strategy for the Preparation of Clickable Peptides and Labeling with 1-(Adomethyl)-4-[18F]-fluorogenzene for PET," Bioconjugate Chem., 2009, 20: 817-523. (Year: 2009).*
Camarero, J.A., "Developing New Tools for the in vivo Generation/Screening of Cyclic Peptide Libraries. A New Combinatorial Approach for the Detection of Bacterial Toxin Inhibitors." LLNL Report, UCRL-TR-227590, 2007, 11 pp.
Cantor, J.,et al., "Biosynthesis of the Cyclotide MCo TI-II using an Engineered Intein," LLNL Report, UCRL-TR-223848, 2006, 12 pp.
Carberry, P., et al., "Fluoride-18 radiolabeling of peptides bearing an aminooxy functional group to a prosthetic ligand via an oxime bond," Bioorganic & Medicinal Chemistry Letters, Oct. 5, 2011, vol. 21, No. 23, pp. 6992-6995.

(Continued)

*Primary Examiner* — Julie Ha
(74) *Attorney, Agent, or Firm* — Brian E. Davy; Bozicevic, Field & Francis LLP

(57) ABSTRACT

Disclosed are knottin peptides containing non-natural amino acids so that they can be formed by chemical conjugation into two or more knottin monomers. The knottin monomers comprise a non-natural amino acid such as an aminooxy residue within the polypeptide sequence. The exemplified dimers were produced by oxime formation between two aldehyde groups present on a polyether linker and an aminooxy functional group that was site-specifically incorporated the knottin. Knottins variants based on EETI (*Ecballium elaterium* trypsin inhibitor) and AgRP (Agouti-related protein) were engineered to contain integrin-binding loops. These dimers were shown to have increased binding strength to integrins on U87MG tumor cells, achieving significant increases in inhibition of cell adhesion and proliferation. Also disclosed are knottin monomers comprising an aminooxy residue; these may be conjugated to molecules such as doxorubicin.

20 Claims, 13 Drawing Sheets

Specification includes a Sequence Listing.

(56) References Cited

OTHER PUBLICATIONS

Christmann, Andreas, et al., "The cystine knot of a squash-type protease inhibitor as a structural scaffold for *Escherichia coli* cell surface display of conformationally constrained peptides," Protein Engineering, 1999, vol. 12, No. 9, pp. 797-806.

Clark, Richard J., et al., "Structural plasticity of the cyclic-cystine-knot framework: implications for biological activity and drug design," Biochem. J., 2006, vol. 394, pp. 85-93.

Copie, Valerie, et al., "Solution Structure and Dynamics of Linked Cell Attachment Modules of Mouse Fibronectin Containing the RGD and Synergy Regions: Comparison with the Human Fibronectin Crystal Structure," J. Mol. Biol. 1998, vol. 277, pp. 663-682.

Daly, Norelle L., et al., "Disulfide Folding Pathways of Cystine Knot Proteins," The Journal of Biological Chemistry, 2003, vol. 278, No. 8, pp. 6314-6322.

DiCara, Danielle, et al., "Structure-Function Analysis of Arg-Gly-Asp Helix Motifs in $\alpha v \Gamma 6$ Integrin Ligands," The Journal of Biological Chemistry, 2007, vol. 28, No. 13, pp. 9657-9665.

Fabritz, Sebastian, e al., "From pico to nano: biofunctionalization of cube-octameric silsesquioxanes by peptides and miniproteins," Org. Biomol. Chem., 2012, vol. 10, pp. 6287-6293.

Gelly, Jean-Christophe, et al., "The KNOTTIN website and database: a new information system dedicated to the knottin scaffold," Nucleic Acids Research, 2004, vol. 32, Database Issue, Oxford University Press, pp. D156-D159.

Hautanen, Aarno, et al., "Effects of Modifications of the RGD Sequence and Its Context on Recognition by the Fibronectin Receptor," The Journal of Biological Chemistry, 1989, vol. 264, No. 3, pp. 1437-1442.

Heitz, Annie, et al., "Knottin cyclization: impact on structure and dynamics," BMC Structural Biology, 2008, 8:54, 19 pp.

Hersel, Ulrich, et al., "RGD modified polymers: biomaterials for stimulated cell adhesion and beyond," Biomaterials, 2003, vol. 24, pp. 4385-4415.

ISR and Written Opinion Int'l. App. No. PCT/US2013/065610, dated Jan. 28, 2014, 15 pp.

Kimura, Richard H., et al., "Engineered Knottin Peptides: A New Class of Agents for Imaging Integrin Expression in Living Subjects," Cancer Research, Mar. 15, 2009, vol. 69, No. 6, pp. 2435-2442.

Kimura, Richard H., et al., "Engineered cystine knot peptides that bind $\alpha v \beta 3$, $\alpha v \beta 5$, and $\alpha 5 \beta 1$ integrins with low-nanomolar affinity," Proteins, Mar. 31, 2009, vol. 77, No. 2, pp. 359-369.

Kraft, Sabine, et al., "Definition of an Unexpected Ligand Recognition Motif for $\alpha v \beta 6$ Integrin," The Journal of Biological Chemistry, 1999, vol. 274, No. 4, pp. 1979-1985.

Lelievre, Dominique, et al., "Synthesis of peptide di-aldehyde precursor for stepwise chemoselective ligations via oxime bonds," Tetrahedron Letters, 2001, vol. 42, pp. 235-238.

Lemieux, George A., et al., "Chemoselective ligation reactions with proteins oligosaccharides and cells," Tibtech, Dec. 1998, vol. 16, pp. 506-551.

Namavari, Mohammad, et al., "A Novel Method for Direct site-specific Radiolabeling of Peptides Using [18F]FDG," Bioconjug Chem., Mar. 2009, vol. 20, No. 3, pp. 432-436.

NCBI, GenBank assession No. 1MR0_A, Oct. 10, 2012.

Schaffer, Lauge, et al., "Assembly of high-affinity insulin receptor agonists and antagonists from peptide building blocks," PNAS, Apr. 15, 2003, vol. 100, No. 8, pp. 4435-4439.

Skerra, Arne, "Engineered protein scaffolds for molecular recognition," J. Mol. Recognit., 2000, vol. 13, pp. 167-187.

Smith, Geoffrey P., et al., "Small Binding Proteins Selected from a Combinatorial Repertoire of Knottins Displayed on Phage," J. Mol. Biol., 1998, vol. 277, pp. 317-332.

\* cited by examiner

4-Formyl benzoic acid (4FB)  4,9-Dioxa-1,12-dodecanediamine (1)

N,N'-((butane-1,4-diylbis(oxy))bis(propane-3,1-diyl))bis(4-formylbenzamide) (2)

N,N'-(3,6,9,12,15,18,21,24,27,30,33,36,39,42,45,48,51,54,57-nonadecaoxanonapentacontane-1,59-diyl)bis(4-formylbenzamide)

SEQUENCE LISTING

```
<160> NUMBER OF SEQ ID NOS: 13

<210> SEQ ID NO 1
<211> LENGTH: 28
<212> TYPE: PRT
<213> ORGANISM: Ecballium elaterium

<400> SEQUENCE: 1

Gly Cys Pro Arg Ile Leu Met Arg Cys Lys Gln Asp Ser Asp Cys Leu
1               5                   10                  15

Ala Gly Cys Val Cys Gly Pro Asn Gly Phe Cys Gly
            20                  25

<210> SEQ ID NO 2
<211> LENGTH: 33
<212> TYPE: PRT
<213> ORGANISM: Artificial sequence
<220> FEATURE:
<223> OTHER INFORMATION: Synthetic polypeptide (EETI 2.5F)

<400> SEQUENCE: 2

Gly Cys Pro Arg Pro Arg Gly Asp Asn Pro Pro Leu Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 3
<211> LENGTH: 33
<212> TYPE: PRT
<213> ORGANISM: Artificial sequence
<220> FEATURE:
<223> OTHER INFORMATION: Synthetic polypeptide (EETI 2.5F_AO)
<220> FEATURE:
<221> NAME/KEY: MISC_FEATURE
<222> LOCATION: (15)..(15)
<223> OTHER INFORMATION: Xaa = aminooxy (AO) residue

<400> SEQUENCE: 3

Gly Cys Pro Arg Pro Arg Gly Asp Asn Pro Pro Leu Thr Cys Xaa Gln
1               5                   10                  15

Asp Ser Asp Cys Leu Ala Gly Cys Val Cys Gly Pro Asn Gly Phe Cys
            20                  25                  30

Gly
```

```
<210> SEQ ID NO 4
<211> LENGTH: 33
<212> TYPE: PRT
<213> ORGANISM: Artificial sequence
<220> FEATURE:
<223> OTHER INFORMATION: Synthetic polypeptide (EETI 2.5D)

<400> SEQUENCE: 4

Gly Cys Pro Gln Gly Arg Gly Asp Trp Ala Pro Thr Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 5
<211> LENGTH: 33
<212> TYPE: PRT
<213> ORGANISM: Artificial sequence
<220> FEATURE:
<223> OTHER INFORMATION: Synthetic polypeptide (EETI 2.5D_AO)
<220> FEATURE:
<221> NAME/KEY: MISC_FEATURE
<222> LOCATION: (15)..(15)
<223> OTHER INFORMATION: Xaa = aminooxy (AO) residue

<400> SEQUENCE: 5

Gly Cys Pro Gln Gly Arg Gly Asp Trp Ala Pro Thr Ser Cys Xaa Gln
1               5                   10                  15

Asp Ser Asp Cys Arg Ala Gly Cys Val Cys Gly Pro Asn Gly Phe Cys
            20                  25                  30

Gly

<210> SEQ ID NO 6
<211> LENGTH: 35
<212> TYPE: PRT
<213> ORGANISM: Artificial sequence
<220> FEATURE:
<223> OTHER INFORMATION: Synthetic polypeptide (AgRP mini)

<400> SEQUENCE: 6

Gly Cys Val Arg Leu His Glu Ser Cys Leu Gly Gln Gln Val Pro Cys
1               5                   10                  15

Cys Asp Pro Ala Ala Thr Cys Tyr Cys Arg Phe Phe Asn Ala Phe Cys
            20                  25                  30

Tyr Cys Arg
        35

<210> SEQ ID NO 7
<211> LENGTH: 38
<212> TYPE: PRT
<213> ORGANISM: Artificial sequence
<220> FEATURE:
<223> OTHER INFORMATION: Synthetic polypeptide (AgRP 7C)

<400> SEQUENCE: 7

Gly Cys Val Arg Leu His Glu Ser Cys Leu Gly Gln Gln Val Pro Cys
1               5                   10                  15

Cys Asp Pro Ala Ala Thr Cys Tyr Cys Tyr Gly Arg Gly Asp Asn Asp
            20                  25                  30

Leu Arg Cys Tyr Cys Arg
        35
```

```
<210> SEQ ID NO 8
<211> LENGTH: 38
<212> TYPE: PRT
<213> ORGANISM: Artificial
<220> FEATURE:
<223> OTHER INFORMATION: synthetic polypeptide (AgRP 7C_AO)
<220> FEATURE:
<221> NAME/KEY: MISC_FEATURE
<222> LOCATION: (38)..(38)
<223> OTHER INFORMATION: Xaa = aminooxy (AO) residue

<400> SEQUENCE: 8

Gly Cys Val Arg Leu His Glu Ser Cys Leu Gly Gln Gln Val Pro Cys
1               5                   10                  15

Cys Asp Pro Ala Ala Thr Cys Tyr Cys Tyr Gly Arg Gly Asp Asn Asp
                20                  25                  30

Leu Arg Cys Tyr Cys Xaa
            35

<210> SEQ ID NO 9
<211> LENGTH: 38
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (38)..(38)
<223> OTHER INFORMATION: X aa= aminooxy (AO) residue

<400> SEQUENCE: 9

Gly Cys Val Arg Leu His Glu Val Cys Leu Gly Gln Gln Val Pro Cys
1               5                   10                  15

Cys Asp Pro Ala Ala Thr Cys Tyr Cys Tyr Gly Arg Gly Asp Asn Asp
                20                  25                  30

Leu Arg Cys Tyr Cys Xaa
            35

<210> SEQ ID NO 10
<211> LENGTH: 47
<212> TYPE: PRT
<213> ORGANISM: Artificial sequence
<220> FEATURE:
<223> OTHER INFORMATION: Synthetic polypeptide (AgRP)

<400> SEQUENCE: 10

Gly Cys Val Arg Leu His Glu Ser Cys Leu Gly Gln Gln Val Pro Cys
1               5                   10                  15

Cys Asp Pro Cys Ala Thr Cys Tyr Cys Arg Phe Phe Asn Ala Phe Cys
                20                  25                  30

Tyr Cys Arg Lys Leu Gly Thr Ala Met Asn Pro Cys Ser Arg Thr
            35                  40                  45

<210> SEQ ID NO 11
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (38)..(38)
<223> OTHER INFORMATION: Xaa = aminooxy (AO) residue

<400> SEQUENCE: 11
```

-continued

```
Gly Cys Val Arg Leu His Glu Ser Cys Leu Gly Gln Gln Val Pro Cys
1               5                   10                  15

Cys Asp Pro Ala Gly Thr Cys Tyr Cys Tyr Gly Arg Gly Asp Asn Asp
                20                  25                  30

Leu Arg Cys Tyr Cys Xaa
            35

<210> SEQ ID NO 12
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (38)..(38)
<223> OTHER INFORMATION: Xaa = aminooxy (AO) residue

<400> SEQUENCE: 12

Gly Cys Val Arg Leu His Glu Ser Cys Leu Gly Gln Gln Val Pro Cys
1               5                   10                  15

Cys Glu Pro Ala Ala Thr Cys Tyr Cys Tyr Gly Arg Gly Asp Asn Asp
                20                  25                  30

Leu Arg Cys Tyr Cys Xaa
            35

<210> SEQ ID NO 13
<211> LENGTH: 33
<212> TYPE: PRT
<213> ORGANISM: Artificial sequence
<220> FEATURE:
<223> OTHER INFORMATION: Synthetic polypeptide (EETI 2.5F_AO_2)
<220> FEATURE:
<221> NAME/KEY: MISC_FEATURE
<222> LOCATION: (33)..(33)
<223> OTHER INFORMATION: Xaa = aminooxy (AO) residue

<400> SEQUENCE: 13

Gly Cys Pro Arg Pro Arg Gly Asp Asn Pro Pro Leu Thr Cys Gln Asp
1               5                   10                  15

Ser Asp Cys Leu Ala Gly Cys Val Cys Gly Pro Asn Gly Phe Cys Gly
                20                  25                  30

Xaa
```

US 11,466,063 B2

CONJUGATED KNOTTIN MINI-PROTEINS CONTAINING NON-NATURAL AMINO ACIDS

CROSS-REFERENCE TO RELATED APPLICATIONS

This application is a continuation of U.S. patent application Ser. No. 15/418,545 filed on Jan. 27, 2017, which is a divisional of U.S. patent application Ser. No. 14/435,711 filed on Apr. 14, 2015, which is a national phase filing of International Patent Application No. PCT/US2013/065610 filed on Oct. 18, 2013, which claims priority from U.S. Provisional Patent Application No. 61/716,363 filed on Oct. 19, 2012, the disclosures of which are hereby incorporated by reference in their entirety.

STATEMENT OF GOVERNMENTAL SUPPORT

This invention was made with Government support under contract CA143498 awarded by the National Institutes of Health. The Government has certain rights in the invention.

BACKGROUND OF THE INVENTION

Field of the Invention

The present invention relates to the field of knottin mini-proteins (also known as cystine-knot peptides), and to the field of chemoselective site-specific oxime conjugation chemistry, in particular incorporating a non-natural amino acid containing an aminooxy side chain, exemplified for use in knottin mini-proteins.

Related Art

The presently exemplified peptides contain engineered (i.e. artificially created) loops having a high binding affinity for cell surface adhesion receptors (e.g. integrins) which can mediate binding to the extracellular matrix (ECM). Altered ECM interactions play an important role in tumorigenesis.[1] Mediated by various receptors, these interactions are often found to enhance tumor proliferation and aggressiveness.[2,3] Integrins, a family of adhesion receptors, bind to components of ECM providing the anchorage that is necessary for cell division, migration, and invasion.[4,5] Several integrins, including αvβ3, αvβ5, and α5β1 are overexpressed in certain types of cancer and tumor vasculature, and therefore inhibitors of these integrins have generated clinical interest.[6-9]

Many integrin receptors bind to an Arg-Gly-Asp (RGD) peptide motif, and the residues around it determine specificity and affinity.[10] Using a RGD motif, different examples of peptides, peptidomimetics, and proteins have been developed for potential cancer therapy, but peptide scaffolds have been less explored for such application. Previously, we developed nanomolar-affinity αvβ3, αvβ5, and αv5β1 integrin binding peptides by evolving a solvent exposed loop of cystine knot peptides, also known as knottins, using yeast surface display.[11,12] The presently exemplified peptides may bind all three of the above integrins, or αvβ3 only, or αvβ3/αvβ5 integrins.

Knottins have a disulfide-bonded framework and triple-stranded beta-sheet fold that often provides remarkable stability in harsh conditions, rendering them as promising candidates as pharmacophoric scaffolds for diagnostic and therapeutic applications.[13,14] Additionally, knottins are attractive for protein engineering, because the disulfide-constrained loops tolerate sequence diversity.[15,16]

Previously, low molecular weight scaffolds, including porphyrins, calixarenes, and carbohydrates have been shown to achieve orders of magnitude increase in binding strength through dimerization. However, larger scaffolds such as peptides that target integrins, have demonstrated only a several fold increase in binding strength with rarely improved therapeutic efficacy.[17-25] Thus, there remains a need in the art for the development of peptides that bind integrins with significantly improved binding affinity.

PATENTS AND PUBLICATIONS

Cochran et al. "Engineered Integrin Binding Peptides," US 2009/0257952, published Oct. 15, 2009, discloses the present engineered integrin-binding knottins, namely EETI 2.5F and 2.5D and AgRP 7C.

Namavari, et al., "A Novel Method for Direct Site-specific Radiolabeling of Peptides Using [18F]FDG," Bioconjug Chem. 2009 March; 20(3): 432-436, discloses a radiolabeled RGD peptide with an aminooxy group. Chemoseletive oxime chemistry was used to provide an easy, one-step synthesis of [18F]FDG-RGG and [18F]FDG-cyclo (RGD$^D$YK) as probes for positron emission tomography of U87MG tumor cells expressing $α_vβ_3$ integrins. The aminooxy group was part of the C terminal end of the peptide and coupled to a labeled fluoro-2-deoxyglucose molecule.

Lemieux, et al., "Chemoselective ligation reactions with proteins, oligosaccharides and cells," TIBTECH, December 1998 (Vol. 16), pp. 506-512, discloses that the reaction of aldehydes or ketones with aminooxy group can form oxime bonds used in the synthesis of multiple peptides. The aminooxy group can be used as a chemoselective coupling partner to ligate proteins. No specific examples of protein ligation using this group are given.

Lelievre, et al., "Synthesis of peptide di-aldehyde precursor for stepwise chemoselective ligations via oxime bonds," Tetrahedron Letters 42 (2001), pp 235-238, discloses a two step process for the synthesis of a tri-branched peptide.

Schaffer et al., "Assembly of high-affinity insulin receptor agonists and antagonists from peptide building blocks," Proc. Nat. Acad. Sci. 100(8):4435-4439 (2003) discloses chemically linked dimers of peptides (S371, S446) that act as insulin receptor agonists. In one approach, the two peptides were prepared recombinantly with glycine/serine linkers; in another approach, they were chemoselectively ligated. A serine was attached to an amino group and subsequently oxidized to an aldehyde function. Triethylene or tetraethylene glycol was functionalized with an oxyamino function at each end and used to chemoselectively ligate two aldehydes by formation of stable oxime bonds.

Hersel et al., "RGD modified polymers: biomaterial for stimulated cell adhesion and beyond," Biomaterials 24:4385-4415 (2003) discloses aminooxy-RGD peptide for coupling to another peptide.

BRIEF SUMMARY OF THE INVENTION

The following brief summary is not intended to include all features and aspects of the present invention, nor does it imply that the invention must include all features and aspects discussed in this summary.

In certain aspects, the present invention concerns engineered knottin proteins (e.g. EETI-II or AgRP) comprising a non-natural amino acid such as an aminooxy (AO) residue that serves to provide a covalent bond to a linker molecule for creating multimeric (e.g. dimeric) peptides. The knottins are preferably engineered to contain a binding sequence for specifically recognizes a target, such as an RGD sequence to bind to integrins flanked by appropriate residues that facilitate binding. The linker molecule is covalently bound to two or more engineered knottins. In certain aspects, the present invention comprises the use of a non-natural amino acid introduced into the knottin for conjugation of an engineered integin binding knottin to another molecule, such as a drug. The exemplified peptide dimers are shown to have increased binding strength to integrin receptor targets. At least one aminooxy (AO) residue is in a scaffold portion of a knottin polypeptide chain, and the knottin further contains a binding loop. The binding loop is composed of an amino acid sequence containing a binding motif, e.g. an RGD motif specific to bind to at least one of $\alpha_v\beta_3$ integrin, $\alpha_v\beta_5$ integrin and $\alpha_5\beta_1$ integrin.

In certain aspects of the present invention, the aminooxy (AO) residue has a side chain that is 2-amino-3-(2-(aminooxy)acetamido)propanoic acid.

In certain aspects of the present invention, the knottin proteins are dimerized through chemical conjugation and a linker molecule. The AO residue contains a side-chain with an aldehyde group, for attachment to the linker molecule. Functional groups binding to aldehydes are incorporated into the linker molecules.

In certain aspects of the present invention, the linker molecule is N,N'-((butane-1,4-diylbis(oxy))bis(propane-3,1-diyl))bis(4-formylbenzamide) (FIG. 1B). The length of the linker molecule is selected to give approximately a 13 angstrom distance between the two knottin subunits within the dimer. This distance helps ensure unhindered interaction of both knottin subunits within the dimer to separate integrin receptors. Other distances may be used.

In certain aspects, the present invention relates to a knottin protein comprising an aminooxy residue conjugated to a small molecule. The small molecule contains a ketone or aldehyde group, or has a linker that contains a ketone or aldehyde group, that reacts with the AO residue for knottin conjugation. In certain aspects of the present invention, the small molecule is a therapeutic anticancer drug, such as doxorubicin, an anthracycline-based chemotherapeutic agent.

DETAILED DESCRIPTION OF THE PREFERRED EMBODIMENT

Definitions

Figure 1A:
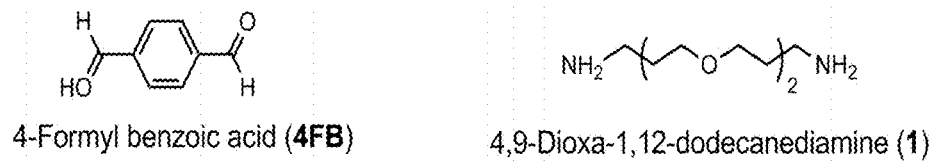
FIG. 1A is a drawing showing a chemical structures for 4-formyl benzoic acid (4FB) and 4,9-dioxa-1,12-dodecanediamine (1), which reacts to yield the dialdehyde linker 2.

The term "scaffold portion" or "molecular scaffold" means a polypeptide or portions thereof having a sequence that is used in combination with a binding loop portion and also having a specific three-dimensional structure, which presents the binding loop portion for optimal target binding. Typically a scaffold portion will be held in place by disulfide linkages between cysteine residues and will be based on a knottin sequence. The binding loop portion is held in place at terminal ends by the molecular scaffold portion. The term "molecular scaffold" has an art-recognized meaning (in other contexts), which is also intended here. For example, a review by Skerra, "Engineered protein scaffolds for molecular recognition," *J. Mol. Recognit.* 2000; 13:167-187 describes the following scaffolds: single domains of antibodies of the immunoglobulin superfamily, protease inhibitors, helix-bundle proteins, disulfide-knotted peptides and lipocalins. Guidance is given for the selection of an appropriate molecular scaffold.

The term "binding loop portion" means a polypeptide having an amino acid sequence of about 9-13 residues. It contains a sequence that is constructed to bind to a target, thereby referred to an engineered loop. It is exogenous to the scaffold portion, which is derived from a knottin. It will further contain a sequence that is engineered to bind to a target, with high affinity, and that the not a knottin native target. For example, a binding loop portion can be created through experimental methods such as directed molecular evolution to bind to a specific ligand. That is, for example, the sequence contains an RGD sequence or the like, flanked by residues that dictate high affinity and specificity. It should be noted that these engineered loops are identified and optimized through combinatorial library screening, or simply grafted entirely from natural binding sequences present within known proteins. The term "specifically recognizes a target" refers to the presence of the binding loop portion having high affinity for binding to another molecule, such as binding to integrins, as described below. The present recognition involves binding at nanomolar concentrations, as exemplified below.

The term "knottin mini-protein", "knottin peptide", or "knottin protein" is used as accepted in the art and refers to a member of a family of small proteins, typically 25-50 amino acids in length, that bind to various molecular targets, including proteins, sugars and lipids. Their three-dimensional structure is minimally defined by a particular arrangement of three disulfide bonds. This characteristic topology forms a molecular knot in which one disulfide bond passes through a macrocycle formed by the other two intrachain disulfide bridges. Although their secondary structure content is generally low, knottins share a small triple-stranded antiparallel β-sheet, which is stabilized by the disulfide bond framework.

Specific examples of knottins include the trypsin inhibitor EETI-II from *Ecballium elaterium* seeds, the neuronal N-type Ca²⁺ channel blocker ω-conotoxin from the venom of the predatory cone snail *Conus geographus*, the Agouti-related protein (See Millhauser et al., "Loops and Links: Structural Insights into the Remarkable Function of the Agouti-Related Protein," *Ann. N.Y. Acad. Sci.*, Jun. 1, 2003; 994(1): 27-35), the omega agatoxin family, etc.

As will be understood from the description below, the knottins referred to herein are modified to contain a non-natural amino acid and an engineered binding loop, e.g. an integrin-binding loop containing the sequence RGD.

The term "amino acid" includes both naturally occurring and synthetic amino acids and includes both the D and L form of the acids. More specifically, amino acids contain up to ten carbon atoms. They may contain an additional carboxyl group, and heteroatoms such as nitrogen and sulfur.

Preferably the amino acids are α and β-amino acids. The term α-amino acid refers to amino acids in which the amino group is attached to the carbon directly attached to the carboxyl group, which is the α-carbon. The term β-amino acid refers to amino acids in which the amino group is attached to a carbon one removed from the carboxyl group, which is the β-carbon. The amino acids described here are referred to in standard IUPAC single letter nomenclature, with "X" means in the present sequence listing, AO.

The non-natural amino acid "AO" is defined in the exemplified sequences as:

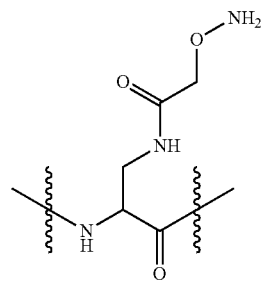 [SMILES: *NC(CNC(=O)CON)C(*)=O]

The term "aminooxy" is defined below as R'—O—NH2.
The term "EETI" means Protein Data Bank Entry (PDB) 2ETI. Its entry in the Knottin database is EETI-II. It has the sequence of SEQ ID NO: 1:

```
                                            (SEQ ID NO: 1)
        GC PRILMR CKQDSDCLAGCVCGPNGFCG
```

The term "AgRP" means PDB entry 1HYK. Its entry in the Knottin database is SwissProt AGRP_HUMAN, where the full-length sequence of 129 amino acids may be found. It comprises the sequence beginning at amino acid 87. An additional G is added to this construct. It also includes a C105A mutation described in Jackson, et al. 2002 *Biochemistry*, 41, 7565.

```
                                           (SEQ ID NO: 10)
GCVRLHESCLGQQVPCCDPCATCYCRFFNAFCYCR-KLGTAMNPCSRT
```

The dashed portion shows a fragment omitted in the "mini" version, below. The bold and underlined portion, from loop 4, is replaced by the engineered binding loop, having RGD sequences described below.

The term includes a "mini"AgRP, in reference to a truncated AgRP that means PDB entry 1MRO. It is also SwissProt AGRP_HUMAN. It has the sequence, similar to that given above,

```
                                            (SEQ ID NO: 6)
         GCVRLHESCLGQQVPCCDPAATCYCRFFNAFCYCR
``` where the italicized "A" represents an amino acid substitution which eliminates a free cysteine. The bold and underlined portion, from loop 4, is replaced by the below described he RGD sequences in binding portions.

The term "cystine" refers to a Cys residue in which the sulfur group is linked to another amino acid though a disulfide linkage; the term "cysteine" refers to the —SH ("half cystine") form of the residue. Binding loop portions may be adjacent to cystines, i.e. there are no other intervening cystines in the primary sequence in the binding loop.

The term "non-natural amino acid" means an amino acid other than the 20 proteinogenic alpha-amino acids which in nature are the building blocks of all proteins within humans and other eukaryotes, and which are also directly encoded by the universal genetic code. Such non-natural amino acids may be obtained commercially, and may be in a protected or unprotected form. See, for examples, the non-natural amino acid products available from HBCChem, Inc. described at http(colon slash slash) hbcchem-inc.com/unnatural_AA.html.

The term "substantial identity" in the context of a peptide indicates that a peptide comprises a sequence with at least 70% sequence identity to a reference sequence, preferably 80%, more preferably 85%, most preferably at least 90% or at least 95% sequence identity to the reference sequence over a specified comparison window, which in this case is either the entire peptide, a molecular scaffold portion, or a binding loop portion (~9-11 residues). Preferably, optimal alignment is conducted using the homology alignment algorithm of Needleman and Wunsch (1970) *J. Mol. Biol.*, 48:443 453. An indication that two peptide sequences are substantially identical is that one peptide is immunologically reactive with antibodies raised against the second peptide. Another indication for present purposes, that a sequence is substantially identical to a specific sequence explicitly exemplified is that the sequence in question will have an integrin binding affinity at least as high as the reference sequence. Thus, a peptide is substantially identical to a second peptide, for example, where the two peptides differ only by a conservative substitution. "Conservative substitutions" are well known, and exemplified, e.g., by the PAM 250 scoring matrix. Peptides that are "substantially similar" share sequences as noted above except that residue positions that are not identical may differ by conservative amino acid changes. As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the NIH Multiple alignment workshop (http colon:slash slash helixweb.nih.gov/multi-align/). Three-dimensional tools may also be used for sequence comparison.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "lower alkyl" means a straight or branched chain hydrocarbon having from one to twelve carbon atoms, optionally substituted with substituents selected from the group consisting of lower alkyl, lower alkoxy, lower alkylsulfanyl, lower alkylsulfenyl, lower alkylsulfonyl, oxo, mercapto, amino optionally substituted by alkyl, carboxy, carbamoyl optionally substituted by alkyl, aminosulfonyl optionally substituted by alkyl, nitro, or lower perfluoroalkyl, multiple degrees of substitution being allowed. Examples of "alkyl" as used herein include, but are not limited to, n-butyl, n-pentyl, isobutyl, and isopropyl, and the like.

The term "alkylene" means a straight or branched chain divalent hydrocarbon radical having from one to ten carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Examples of "alkylene" as used herein include, but are not limited to, methylene, ethylene, n-propylene, n-butylene, and the like.

As used herein, the term "alkyl" refers to a straight or branched chain hydrocarbon having from one to twelve carbon atoms, optionally substituted with substituents selected from the group consisting of lower alkyl, lower alkoxy, lower alkylsulfanyl, lower alkylsulfenyl, lower alkylsulfonyl, oxo, mercapto, amino optionally substituted by alkyl, carboxy, carbamoyl optionally substituted by alkyl, aminosulfonyl optionally substituted by alkyl, nitro, or lower perfluoroalkyl, multiple degrees of substitution being allowed. Examples of "alkyl" as used herein include, but are not limited to, n-butyl, n-pentyl, isobutyl, and isopropyl, and the like.

As used herein, the term "alkoxy" means the group $R_aO$—, where $R_a$ is alkyl as defined above and the term "$C_1$-$C_2$ alkoxy" means the group $R_aO$—, where $R_a$ is $C_1$-$C_2$ alkyl as defined above.

"Haloalkyl" refers to a straight or branched chain hydrocarbon containing at least 1, and at most 4, carbon atoms substituted with at least one halogen, halogen being as defined herein. Examples of branched or straight chained "$C_1$-$C_4$ haloalkyl" groups useful in the present invention include, but are not limited to, methyl, ethyl, propyl, isopropyl, isobutyl and n-butyl substituted independently with one or more halogens, e.g., fluoro, chloro, bromo and iodo.

As used herein, the term "haloalkoxy" means the group $R_aO$—, where $R_a$ is haloalkyl as defined above and the term "$C_1$-$C_2$ haloalkoxy" means the group $R_aO$—, where $R_a$ is $C_1$-$C_2$ haloalkyl as defined above.

The term "aryl" refers to an optionally substituted benzene ring or to an optionally substituted benzene ring system fused to one or more optionally substituted benzene rings to form, for example, anthracene, phenanthrene, or napthalene ring systems. Exemplary optional substituents include lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. Examples of "aryl" groups include, but are not limited to, phenyl, 2-naphthyl, 1-naphthyl, biphenyl, as well as substituted derivatives thereof. As used herein, the term "aralkyl" refers to an aryl or heteroaryl group, as defined herein including both unsubstituted and substituted versions thereof, attached through a lower alkylene linker, wherein lower alkylene is as defined herein. As used herein, the term "heteroaralkyl" is included within the scope of the term "aralkyl". The term heteroaralkyl is defined as a heteroaryl group, as defined herein, attached through a lower alkylene linker, lower alkylene is as defined herein. Examples of "aralkyl", including "heteroaralkyl", include, but are not limited to, benzyl, phenylpropyl, 2-pyridinylmethyl, 4-pyridinylmethyl, 3-isoxazolylmethyl, 5-methyl-3-isoxazolylmethyl, and 2-imidazoyly ethyl.

As used herein the term "aralkoxy" means the group $R_bR_aO—$, where $R_a$ is alkylene and $R_b$ is aryl, both as defined above.

As used herein, the term "alkylsulfanyl" means the group $R_aS—$, where $R_a$ is alkyl as defined above.

As used herein, the term "alkylsulfenyl" means the group $R_aS(O)—$, where $R_a$ is alkyl as defined above.

As used herein, the term "alkylsulfonyl" means the group $R_aSO_2—$, where $R_a$ is alkyl as defined above.

As used herein, the term "oxo" means the group =O

As used herein, the term "mercapto" means the group —SH.

As used herein, the term "carboxy" means the group —COOH.

The term "polypeptoid" means a polymer of peptoids, i.e. N-substituted glycines, as further described in Kirshenbaum et al., "Sequence-specific polypeptoids: A diverse family of heteropolymers with stable secondary structure," Proc. Nat. Acd. Sci. 95(8): 4303-4308 (1998)

General Overview

The present invention relates to compositions and methods for providing a simple and efficient way to increase the binding strength of small engineered peptides such as knottin mini-proteins. A non-natural amino acid residue, containing an aminooxy (AO) side-chain, was incorporated into the native peptide backbone of two different classes of knottin scaffolds, *Ecballium elaterium* trypsin inhibitor (EETI) and the Agouti-related protein (AgRP).

As described above, knottin mini-proteins have a characteristic disulfide-bonded structure, which is illustrated in Gelly et al., "The KNOTTIN website and database: a new information system dedicated to the knottin scaffold," *Nucleic Acids Research*, 2004, Vol. 32, Database issue D156-D159. A triple-stranded β-sheet is present in many knottins. The spacing between Cys residues is important, as is the molecular topology and conformation of the RGD-containing integrin binding loop. These attributes are critical for high affinity integrin binding. The RGD mimic loop is inserted between knottin Cys residues, but the length of the loop must be adjusted for optimal integrin binding depending on the three-dimensional spacing between those Cys residues. For example, if the flanking Cys residues are linked to each other directly, the optimal loop may be shorter than if the flanking Cys residues are linked to Cys residues separated in primary sequence. Otherwise, particular amino acid substitutions can be introduced that constrain a longer RGD-containing loop into an optimal conformation for high affinity integrin binding.

Engineered integrin-binding variants of EETI and AgRP were site-selectively dimerized through a linker molecule, such as a polyether linker modified to contain two aldehyde groups (N,N'-((butane-1,4-diylbis(oxy))bis(propane-3,1-diyl))bis(4-formylbenzamide)). The conjugation chemistry is based on the chemoselective reaction of AO groups with aldehydes to form oxime groups. The present invention also relates to oxime-based conjugation of knottin mini-proteins to small molecules, such as drugs or imaging labels. The linker may be any suitable polymeric chain, including polyether, alkyl chain, polypeptide, β-peptide, or polypeptoid.

Knottin Mini-Protein Structures

The present knottin mini-proteins comprise a molecular scaffold portion. They are generally held in a rigid three dimensional conformation by disulfide bonds formed between two cystine residues. Loop portions exist between the cystines.

Characteristics of a desirable scaffold for protein design and engineering include: 1) high stability in vitro and in vivo, 2) the ability to replace amino acid regions of the scaffold with other sequences without disrupting the overall fold, 3) the ability to create multifunctional or bispecific targeting by engineering separate regions of the molecule, and 4) a small size to allow for chemical synthesis and incorporation of non-natural amino acids if desired. Scaffolds derived from human proteins are favored for therapeutic applications to reduce toxicity or immunogenicity concerns, but are not always a strict requirement. Other scaffolds that have been used for protein design include fibronectin (Koide et al., 1998), lipocalin (Beste et al., 1999), cytotoxic T lymphocyte-associated antigen 4 (CTLA-4) (Hufton et al., 2000), and tendamistat (McConnell and Hoess, 1995; Li et al., 2003). While these scaffolds have proved to be useful frameworks for protein engineering, molecular scaffolds such as knottins have distinct advantages over other molecular scaffolds.

Chemoselective Chemistry

Chemical strategies frequently used for protein or peptide conjugation rely on amine- or thiol-based reactivity endogenous to the 20 genetically encoded amino acids. However, it is often difficult to produce homogeneous and site-selective conjugation products using these approaches. Multiple reactive amines (Lysine and N-terminal amino groups) are present in proteins and peptides, and redox active cysteines can have unpredictable and undesirable effects on protein folding and stability.

Figure 1A:
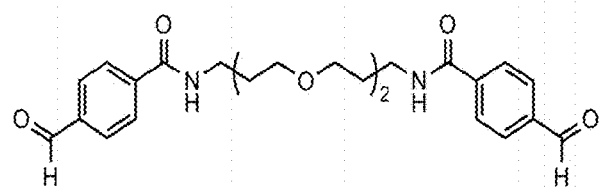

The present invention exploits the chemoselective formation of an oxime bond between an aldehyde and an aminooxy functional group, neither of which are found in genetically-encoded amino acids.[24,27-29] An oxime is formed by condensation of an aminooxy group with either an aldehyde or a ketone, as shown in FIG. 1. The basic scheme for oxime conjugation is as follows:

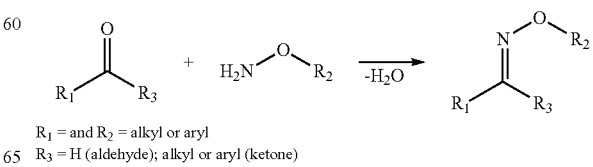

$R_1$ = and $R_2$ = alkyl or aryl
$R_3$ = H (aldehyde); alkyl or aryl (ketone)

The above chemistry is exploited in the present invention by providing a knottin with an amino acid having a non-natural side chain. The side chain will have one of the shown groups, so that another moiety (such as a small molecule, monomer peptide, or linker) can be conjugated by means of the side chain. In the examples shown in FIGS. 1A and 1B, the peptide is engineered to contain a side chain with aminooxy group, and a linker is prepared to have ends with aldehydes, specifically benzamides.

In particular, the aminooxy residue exemplified in the present invention is 2-amino-3-(2-(aminooxy)acetamido)propanoic acid, which has the following structure and is denoted here as residue "AO" in various sequences described:

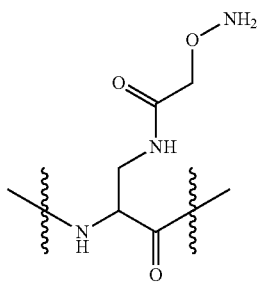 [SMILES: *NC(CNC(=O)CON)C(*)=O]

As shown above, this residue is incorporated into the knottin polypeptide chain using standard methods for Fmoc-based solid phase peptide synthesis.

As can be seen above, the amino acid side chain may be represented as —CH$_2$—NH—C(=O)—CH$_2$—O-NH$_2$. The required aminooxy group is bolded and underlined. Various modifications may be employed in the CH$_2$—NH—C(=O)—CH$_2$ portion of the side chain, and may be represented using the general formula R'—O—NH$_2$, where R' is lower alkyl, alkylene, aryl, alkoxy, haloalkyl, haloalkoxy, aralkoxy, alkylsulfanyl, alkylsulfenyl, or alkylsulfonyl.

The present knottin peptides will generally have about 25-50 amino acid residues and so may be prepared by solid phase peptide synthesis or equivalent methods. See, e.g. Collins "Water Soluble Solid Phase Peptide Synthesis," US 2012/0041173, published Feb. 16, 2012.

Methods of synthesis that allow for the incorporation of non-natural amino acids may be employed, such as described in Shen et al., "Umpolumng reactivity in amide and peptide synthesis," Nature 465; 1027-1032 (24 Jun. 2010).

Using solid phase peptide synthesis (SPPS), a non-natural amino acid with either an aminooxy or an aldehyde group can be incorporated at different knottin sequence positions to allow for a variety of linking sites. Knottin dimers produced through oxime-based chemistry can contain linkers of varying lengths to alter or optimize biological properties. Non-naturals may also be included into the present peptides by mutagenesis, as described, e.g. in Hohsaka et al, "Incorporation of non-natural amino acids into proteins," Curr. Opinion in Chemical Biology, 6:809-815 (2002).

The present non-natural amino acids will contain a side chain that may be coupled to a linker; as such, they may contain a side chain that is aminooxy, aldehyde, ketone, alkyne, alkene, aryl halide diene or azide. Guidance for use of such amino acids may be found in U.S. Pat. No. 6,858,396 to Dix, entitled "Positively charged non-natural amino acids, methods of making and using thereof in peptides", issued Feb. 22, 2005; Mao et al. U.S. Pat. No. 8,048,988, issued Nov. 1, 2011, entitled "Compositions containing, methods Involving, and uses of non-natural amino acids and peptides." In other embodiments, the present peptides may contain side chains that are aminooxy, aldehyde, ketone, alkyne, azide, alkene, aryl halide, or diene. In other embodiments, the present peptides may contain side chains that are aminooxy, aldehyde, or ketone.

The side chain used will be selected to be easily reacted with a specific reactive group contained in a linker. The linker will have functional groups on its ends that react with the side chain of each non-natural amino acid used.

Furthermore, knottins containing non-natural amino acids according to the present invention can be conjugated to a therapeutic molecule for drug delivery. Such small molecules can have an aldehyde or ketone group, or a linker that contains an aldehyde or ketone group, to react with the aminooxy group present within the knottin.

Knottins Prepared as Dimers

Aminooxy residues were incorporated into two different classes of knottins for oxime-based dimerization: *Ecballium elaterium* trypsin inhibitor (EETI) and a truncated form of the Agouti-related protein (AgRP). Knottin variants contain an aminooxy residue along with an RGD integrin binding sequence.

EETI was modified as follows:

```
                                                (SEQ ID NO: 1)
GC PRILMR [CKQDSDC*]LAGCV[CGPNGFC**]G.
```

The bold and underlined portion is replaced with a binding portion. As illustrated below, an integrin-binding sequence(s) containing the RGD motif is used instead as this portion. Additional loops, identified here as loops 2(*) and 3(**), are shown in brackets. These loops are part of the scaffold portion can also be varied without affecting binding efficiency, as is demonstrated below. AS can be seen, they are delimited by C residues.

EETI 2.5F was evolved from EETI to have specificity for αvβ3, αvβ5, and α5β1 integrin with antibody-like affinity.[11] In previous studies, a K15S mutation allowed site-specific attachment of molecular imaging probes to the knottin N-terminus.

```
EETI 2.5F:
                                                (SEQ ID NO: 2)
GCP₁R₂P₃RGDN₇P₈P₉L₁₀T₁₁CKQDSDCLAGCVCGPNGFCG
```

Again, the bolded portion is the binding portion. The following sequences contain a non-natural AO instead of K at position just carboxy to the binding sequence, which is numbered as 1-11.

```
EETI 2.5F_AO:
                                                (SEQ ID NO: 3)
GCPRPRGDNPPLTCXQDSDCLAGCVCGPNGFCG
```

Another variant was constructed, based on EETI 2.5D, which binds αvβ3 and αvβ5 integrin:

```
EETI 2.5D:
                                                (SEQ ID NO: 4)
GCPQGRGDWAPTSCKQDSDCRAGCVCGPNGFCG
```

```
EETI 2.5D_AO:
                                        (SEQ ID NO: 5)
GCPQGRGDWAPTSCXQDSDCRAGCVCGPNGFCG
```

Again, the binding portions are the binding portions. AgRP 7C is a 38-amino acid knottin peptide evolved from a truncated cystine-knot domain of AgRP to have antibody-like affinity for αvβ3 integrin.[12] This referenced paper discloses a truncated form of the Agouti-related protein (AgRP), a 4-kDa knottin peptide with four disulfide bonds and four solvent-exposed loops, used as a scaffold to engineer peptides that bound to $\alpha_v\beta_3$ integrins with high affinity and specificity.

Truncated AgRP: GCVRLHESCLGQQVPCCDPAATCY CRFFNAF CYCR (SEQ ID NO: 6). The bolded portion is replaced by the binding portions.

```
AgRP 7C:
                                        (SEQ ID NO: 7)
GCVRLHESCLGQQVPCCDPAATCYCYGRGDNDLRCYCR

AgRP 7C_AO:
                                        (SEQ ID NO: 8)
GCVRLHESCLGQQVPCCDPAATCYCYGRGDNDLRCYCX
```

The present peptides can be produced by recombinant DNA methods or by solid phase peptide synthesis, which has been demonstrated for both classes of knottins described here. These peptides can be conjugated through their N-termini to other molecules containing amine-reactive groups, such as fluorescent dyes, radioisotopes, or small molecule drugs. Still further, these peptides may be synthesized with non-natural amino acids that allow for additional crosslinking functionality, such as alkyne or azide groups used in Huisgen cycloaddition ("click") chemistry. Crosslinked polystyrene resin containing Rink amide linkers, such as TentaGel S RAM Fmoc resin, (Advanced ChemTech) may be used to give a C-terminal amide upon cleavage. Peptides are cleaved from the resin and side-chains are deprotected with 8% trifluoroacetic acid, 2% triisopropylsilane, 5% dithiothreitol, and the final product is recovered by ether precipitation. Modified amino acids such as B-alanine are used as the N-terminal amino acid to prevent thiazolidone formation and release of fluorescein during peptide deprotection (Hermanson, 1996). Peptides are purified by reverse phase HPLC using an acetonitrile gradient in 0.1% trifluoroacetic acid and a C4 or C18 column (Vydac) and verified using matrix-assisted laser desorption/ionization time-of-flight mass spectrometry (MALDI-TOF) or electrospray ionization-mass spectrometry (ESI-MS).

The peptides specifically set forth herein may be modified in a number of ways. For example, the peptides may be further crosslinked internally, or may be crosslinked to each other, or the RGD-containing loops may be grafted onto other crosslinked molecular scaffolds. There are a number of commercially-available cross-linking reagents for preparing protein or peptide bioconjugates. Many of these crosslinkers allow dimeric homo- and heteroconjugation of biological molecules through free amine or sulfhydryl groups in protein side chains. More recently, other crosslinking methods involving coupling through carbohydrate groups with hydrazide moieties have been developed. These reagents have offered convenient, facile, crosslinking strategies for researchers with little or no chemistry experience in preparing bioconjugates.

Dimerization/Multimerization and Linkage

The present knottin monomers are linked to each other and/or to other molecules by means of the incorporation of a reactive residue within the chain of the monomer at a position determined to be on the surface of the folded peptide. The reactive residue contains an aminooxy group pendant to the peptide chain; the aminooxy group provides a basis for an oxime linkage to another molecule, i.e. a "linking molecule," group containing an aldehyde or ketone group. The linking molecule has two reactive aldehyde groups for the preparation of a dimer of aminooxy-containing knottins; branched linking molecules may be used for higher order knottin clusters, e.g. trimers, tetramers, pentamers, etc. The linker molecules is chosen to provide a spacer between knottins to allow the engineered binding loop on each knottin to interact with the cognate ligand, e.g. the ability of RGD in a binding loop to bind to αvβ3 integrin on a tumor cell.

As discussed below, the selection of linker spacing and linker site provided here allows "clustering" of knottin peptides and a surprising level of binding enhancement of the multimer to the target. A linker as exemplified in FIG. 1A has a diamine portion of 13 Angstroms and 17.3 Angstroms in the overall linker shown at compound 2. was used in the present examples; linkers are generally chosen to contain flexible chains of about 20-100 atoms, and may comprise aliphatic and aromatic groups in a chain.

The AO group of the present knottins may also be used for conjugation to a variety of small molecules, in particular anti-cancer drugs. As discussed below in connection with FIG. 5, an anthracycline antibiotic (doxorubicin) having a —C(=O)CH$_2$OH structure is coupled to the knottin through the keto group. Other molecules, including the many known analogs of doxorubicin may be coupled to the present knottins in this way.

EXAMPLES

Example 1: Knottin Monomers

The aminooxy group was substituted for Lys15 in EETI2.5F and Arg38 in AgRP7C since previous studies demonstrated flexibility of these positions.[11,30] See SEQ ID NOs; 3, 5 and 8.

These knottin monomers were prepared by incorporating the aminooxy residue 2-amino-3-(2-(aminooxy)acetamido) propanoic acid into the polypeptide using solid phase peptide synthesis with an Fmoc-protected version.

Example 2: Dimerization of Knottin Monomers

Because various lengths of diamine chains were readily available from vendors, the dialdehyde cross-linkers were prepared by conjugating two 4-formyl benzoic acid groups (4FB) to a diamine chain (FIG. 1A, 1B). 4,9-Dioxa-1,12-dodecanediamine (1) was chosen as the diamine chain to provide up to an approximately 13 Å distance between two covalently linked knottins since a shorter spacer length may hinder the dimeric interaction between the ligand and the receptor.[21,25] 4FB was coupled to 1 with dicyclocarbodiimide and HOBt in CH$_2$Cl$_2$ at 0° C. for 2 h.

Figure 1B:
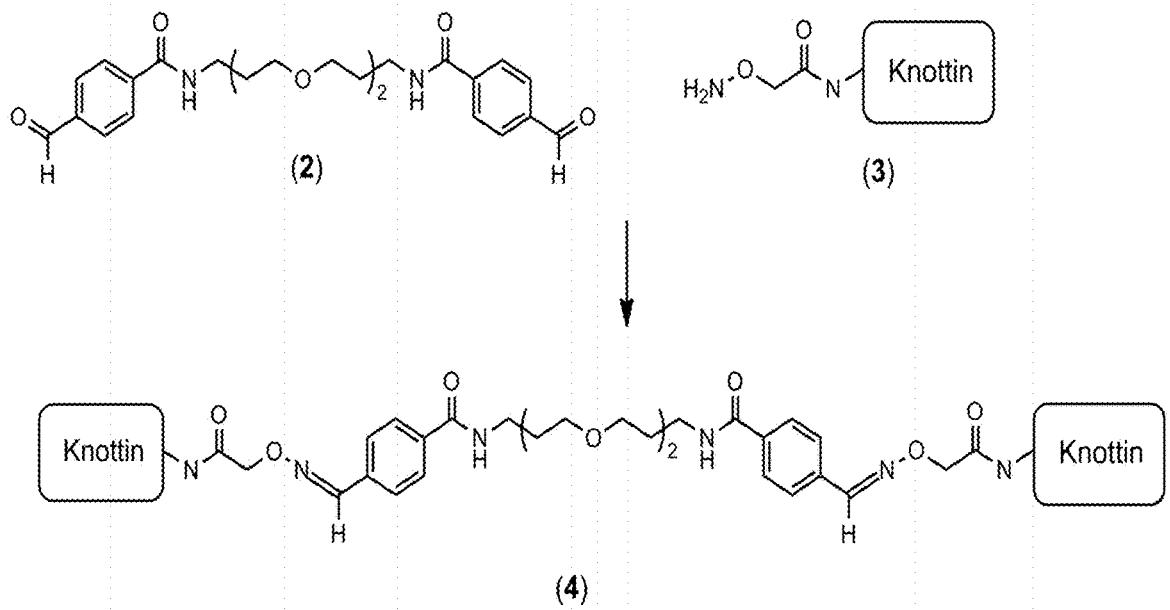
FIG. 1B is a schematic representation of oxime ligation of 2 and 3 to yield the dimeric knottin 4.

The compound 2 was purified with reverse phase HPLC (RP-HPLC) in 76% yield and conjugated to knottins containing an aminooxy residue (3) in phosphate buffer at 25° C. (FIG. 1B). After 1.5 h of incubation, the dimeric knottins (4) were purified with RP-HPLC in 96% yield (Table 1).

TABLE 1

Characteristics of knottin monomers and dimers

| Peptide | RP-HPLC[a] $R_t$ (min) | ESI-MS[b] $[M + H]^+_{calc}$ | $[M + H]^+_{exp}$ |
|---|---|---|---|
| Dialdehyde linker | 33.2 | 469.5 | 469.3 |
| EETI 2.5F_AO | 17.6 | 3365.6 | 3365.4 |
| EETI 2.5F-Dimer | 23.9 | 7162.7 | 7160.4 |
| AgRP 7C_AO | 18.5 | 4225.8 | 4226.3 |
| AgRP 7C Dimer | 22.3 | 8883.1 | 8883.0 |
| FNRDG_AO | 18.4 | 3178.3 | 3177.8 |
| FNRDG-Dimer | 23.9 | 6789.1 | 6788.0 |

[a]The gradient used for RP-HPLC is 10-60% solvent B (90% acetonitrile/10% water/0.1% trifluoroacetic acid) over 38 min.
[b]Molecular masses were determined by electrospray ionization mass spectrometry (ESI-MS).

Example 3: Competition Binding Assay

Figure 2A:
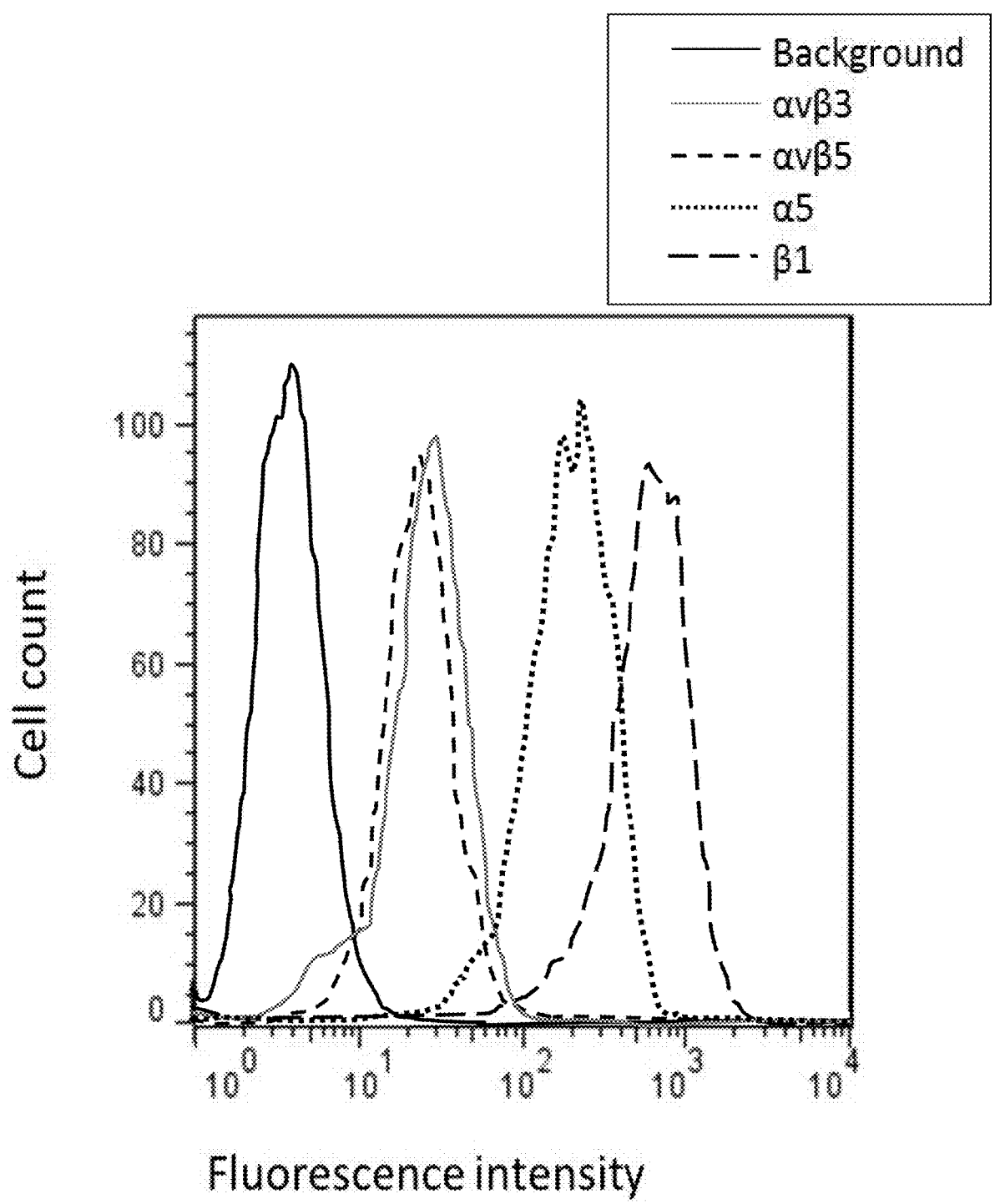
FIG. 2A are flow cytometry histograms showing integrin ($\alpha v\beta 3$, $\alpha v\beta 5$, $\alpha 5$, and $\beta 1$) expression on U87MG cells, a recognized cancer cell model (human glioblastoma-astrocytoma, epithelial-like cell line), as measured using integrin-specific antibodies. Since the $\alpha 5$ subunit can only pair with the $\beta 1$ subunit, the $\alpha 5$ histogram represents the amount of $\alpha 5\beta 1$ integrin complex expressed on the cell surface.
Figure 2B:
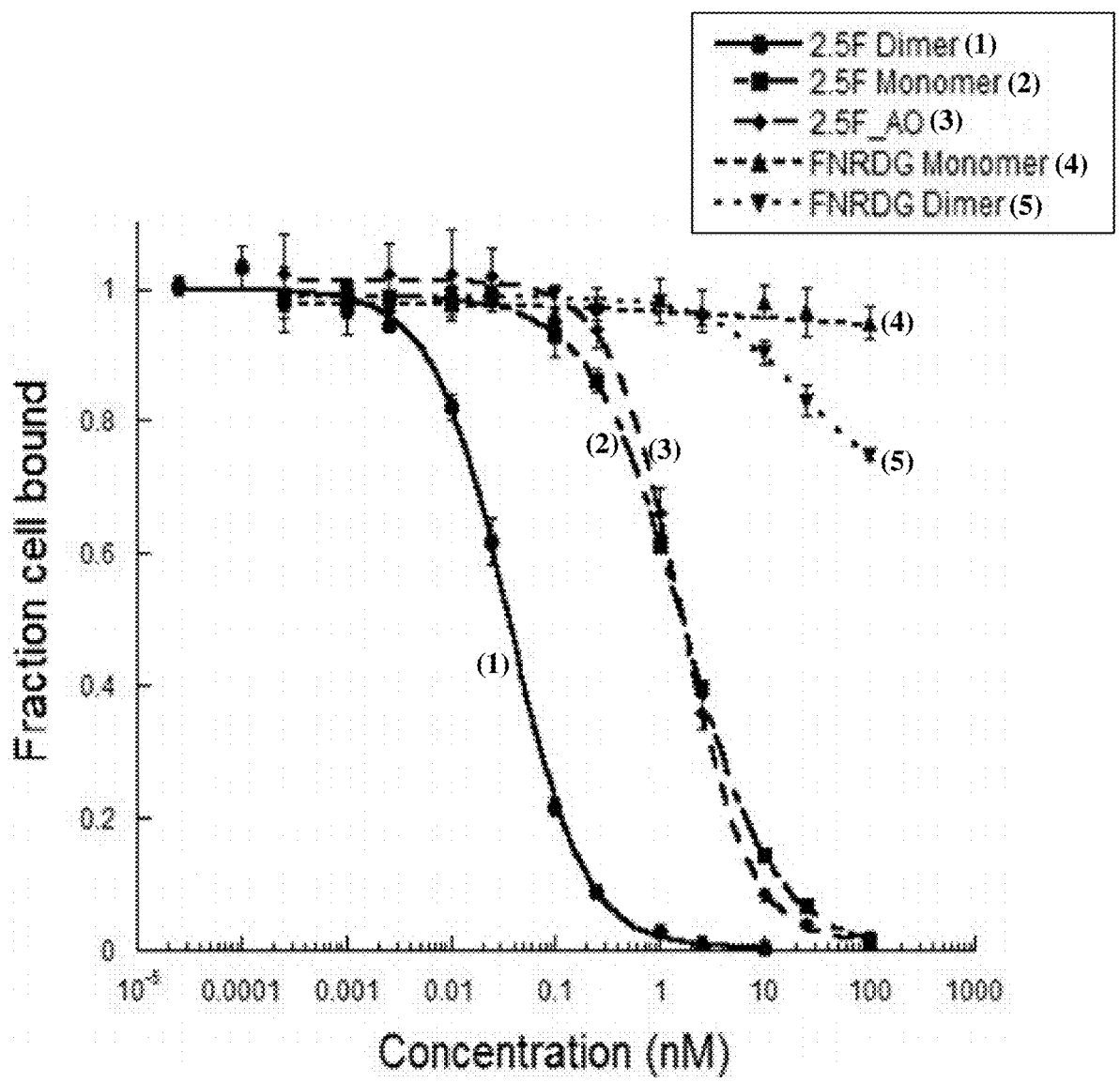
FIG. 2B is a graph showing a competition assay of EETI-based integrin binding proteins 2.5F dimer and 2.5F monomer to U87MG cells, as measured by flow cytometry. Alexa488-labeled EETI 2.5F was used as a competitor. Monomeric EETI 2.5F with an introduced aminooxy residue is designated as 2.5F_AO. EETI-based peptides containing a scrambled sequence that does not bind integrin (FNRDG monomer and FNRDG dimer) are shown as negative controls.
Figure 2C:
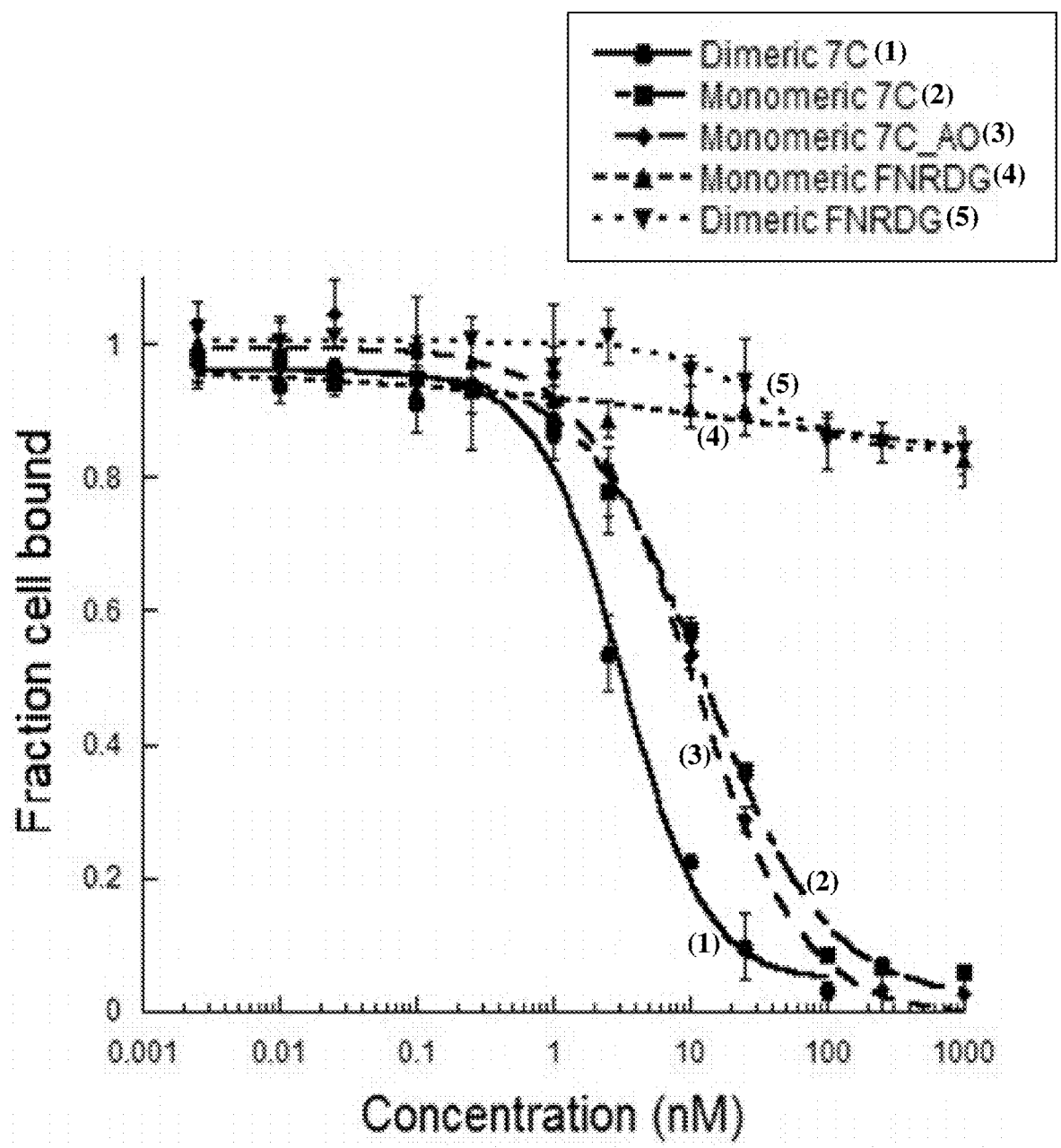
FIG. 2C is a graph showing a competition assay of AgRP-based integrin binding proteins: dimeric 7C and monomeric 7C to U87MG cells, as measured by flow cytometry. Alexa488-labeled AgRP 7C was used as a competitor. Monomeric AgRP 7C with aminooxy residue is designated as Monomeric 7C_AO. EETI-based peptides containing a scrambled sequence that does not bind integrin (monomeric FNRDG and dimeric FNRDG) are shown as negative controls.

Competition binding assays were performed to measure the relative binding affinities of engineered knottins to U87MG cells expressing $\alpha v \beta 3$, $\alpha v \beta 5$, and $\alpha 5 \beta 1$ integrins (FIG. 2A, 2B, 2C). $2 \times 10^5$ U87MG cells were incubated at 4° C. for 10 h in integrin binding buffer (20 mM Tris pH 7.5, 1 mM $MgCl_2$, 1 mM $MnCl_2$, 2 mM $CaCl_2$, 100 mM NaCl, and 0.1% BSA) and varying concentrations of the peptides with 0.25 nM of Alexa488-labeled EETI 2.5F as a competitor for dimeric and monomeric EETI 2.5F, and 5 nM of Alexa488-labeled AgRP 7C as a competitor for dimeric and monomeric AgRP 7C. Half-maximal inhibitory concentration ($IC_{50}$) values were determined by nonlinear regression analysis using KaleidaGraph (Synergy Software), and are presented as the average of three separate experiments.

As shown by the $IC_{50}$ values, the apparent binding binding affinities of EETI2.5F and AgRP7C dimers increased by approximately 46- and 4-fold compared to the monomers, respectively (Table 2).

TABLE 2

U87MG cell binding and adhesion data

| Ligand | Binding $IC_{50}$ (nM) | Adhesion $EC_{50}$ (nM) |
|---|---|---|
| EETI 2.5F | 1.64 ± 0.03 | 180 ± 14 |
| EETI 2.5F_AO | 1.57 ± 0.05 | N.D. |
| EETI 2.5F Dimer | 0.036 ± 0.002 | 8 ± 2 |
| AgRP7 C | 13 ± 1 | N.D. |
| AgRP 7C Dimer | 3.2 ± 0.6 | N.D. |
| FNRDG_AO | (---) | (---) |
| FNRDG Dimer | (---) | (---) |

$IC_{50}$ values from competition binding assays (FIG. 2) and $EC_{50}$ values cell adhesion assays (FIG. 3) are summarized. (---) indicates very weak to no competition. N.D.=not determined
The scrambled EETI FNRDG monomer and dimer showed negligible binding, indicating that the binding observed is due to the specific interaction between the knottins and the integrins.

Example 4: Inhibition of Integrin-Dependent Cell Adhesion

Figure 3A:
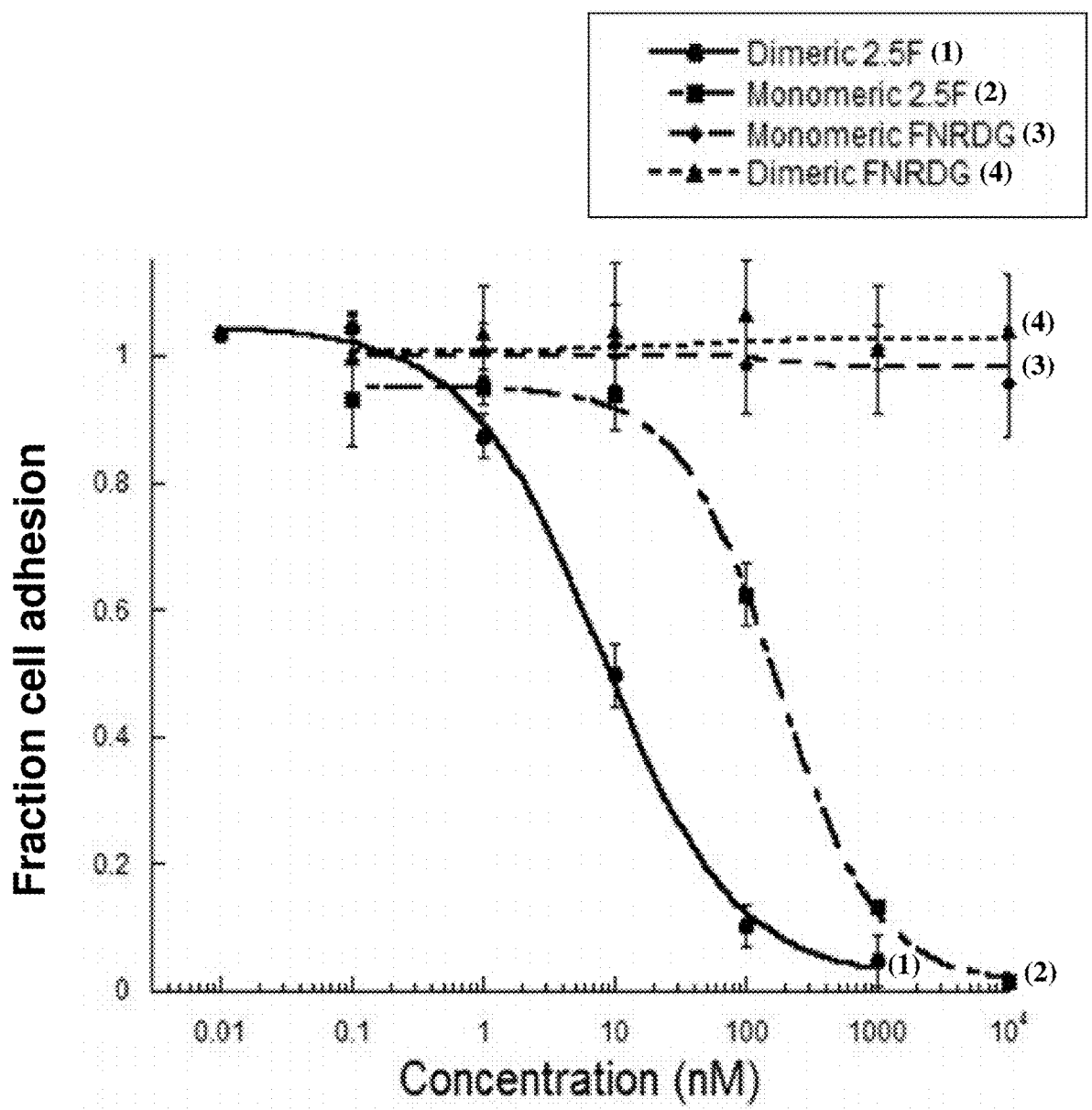
FIG. 3A is a graph measuring comparative inhibition of adhesion of U87MG cells treated with dimeric and monomeric 2.5F to fibronectin, a component of ECM. Fibronectin coated plates were incubated with U87MG cells with the indicated concentrations of peptides. Adherent cells remaining after several wash steps were quantified with crystal violet staining by absorbance at 600 nm. EETI-based peptides containing a scrambled sequence that does not bind integrin (monomeric FNRDG and dimeric FNRDG) are shown as negative controls. Values were normalized to negative control containing no competing peptides.

Since the EETI 2.5F dimer showed remarkable improvement in integrin binding strength we analyzed its ability to block interaction between U87MG cells and fibronectin through a cell adhesion assay (FIG. 3A). Fibronectin is known to interact with $\alpha v \beta 3$, $\alpha v \beta 5$, and $\alpha 5 \beta 1$ integrins, and our previous study showed that EETI 2.5F effectively blocks these interactions and detaches cells from fibronectin coated plates.

Varying concentrations of peptides were added to $4 \times 10^4$ cells in 100 µl of IBB, incubated for 1 h at 37° C., 5% $CO_2$, and gently washed with Dulbecco's PBS (DPBS, Invitrogen). Remaining adherent cells were incubated with 100 µl of 0.2% crystal violet and 10% ethanol for 10 min at room temperature, washed in DPBS and solubilized with 100 µl/well of a 50:50 mixture of 100 mM sodium phosphate, pH 4.5 and ethanol for 10 min. The absorbance at 600 nm was measured using Synergy HT microplate reader (BioTek).

Figure 3B:
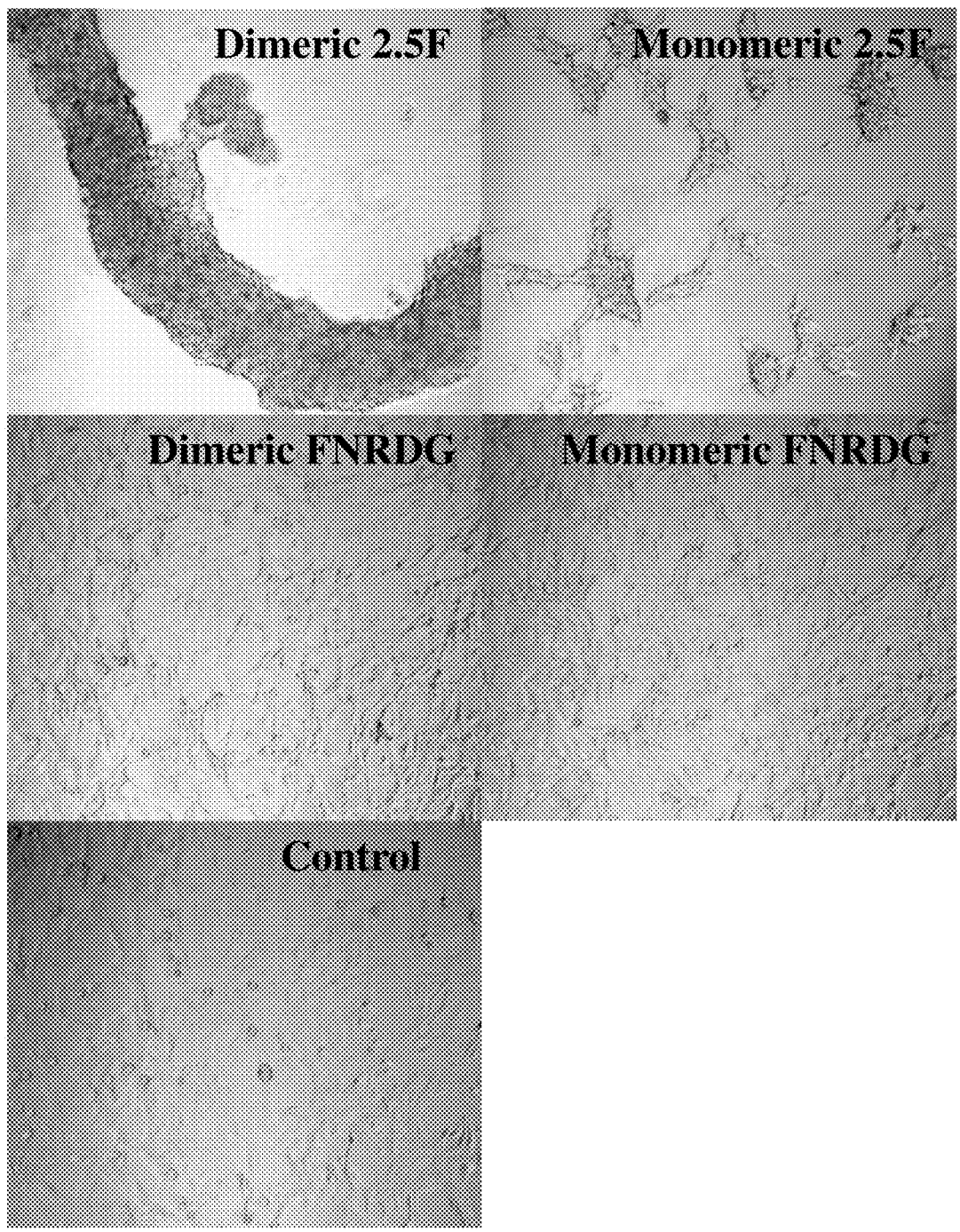
FIG. 3B is a panel of microscope images of the U87MG cells on culture plates after 24 h treatment with 500 nM of the indicated knottins.

Both EETI 2.5F monomer and dimer were able to inhibit U87MG cell adhesion to fibronectin-coated plates in a dose-dependent manner. As shown by the $IC_{50}$ values, EETI 2.5F dimer was 100-fold more effective in preventing U87MG cell adhesion compared to the monomer, while the scrambled FNRDG monomer and dimer controls were not able to inhibit cell adhesion (Table 2). When incubated in the presence of 500 nM of EETI 2.5F monomer and dimer for 24 h in DMEM media with 4% FBS, U87MG cells exhibited a rounded morphology (FIG. 3B).

Example 5: Cytotoxicity of EETI 2.5F Monomer and Dimer with U87MG Cells

To demonstrate the cytotoxicity of the EETI 2.5F monomer and dimer, U87MG cells were incubated in medium containing 4% FBS with 1 µM of the knottins on fibronectin coated plates, and the cell viability was determined after 24, 48, and 72 hours of treatment using AlamarBlue indicator reagent (Invitrogen).

Figure 4A:
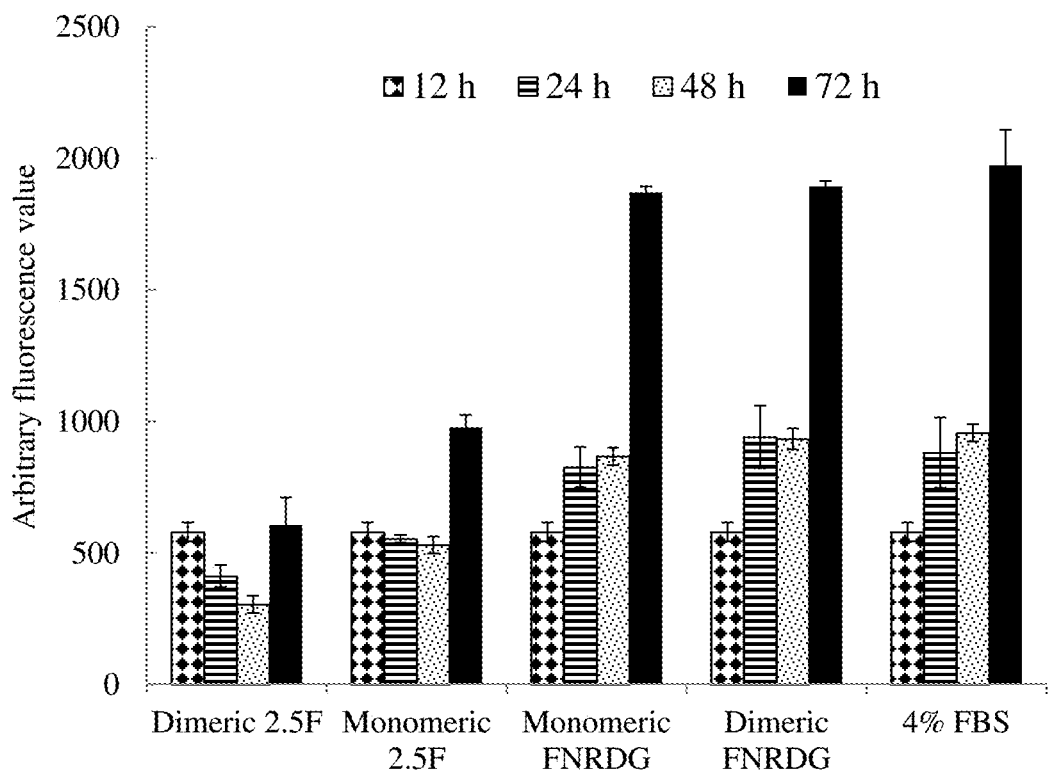
FIG. 4A is a bar graph showing time dependent cytotoxicity of U87MG cells after treatment with the indicated knottin mini-proteins. Cytotoxicity was monitored by incubating U87MG cells on culture plates with 500 nM of each knottin in 4% FBS media at 37° C. and 5% $CO_2$ and measuring cell viability at 24, 48, and 72 h after the treatment using the AlamarBlue indicator dye.
Figure 4B:
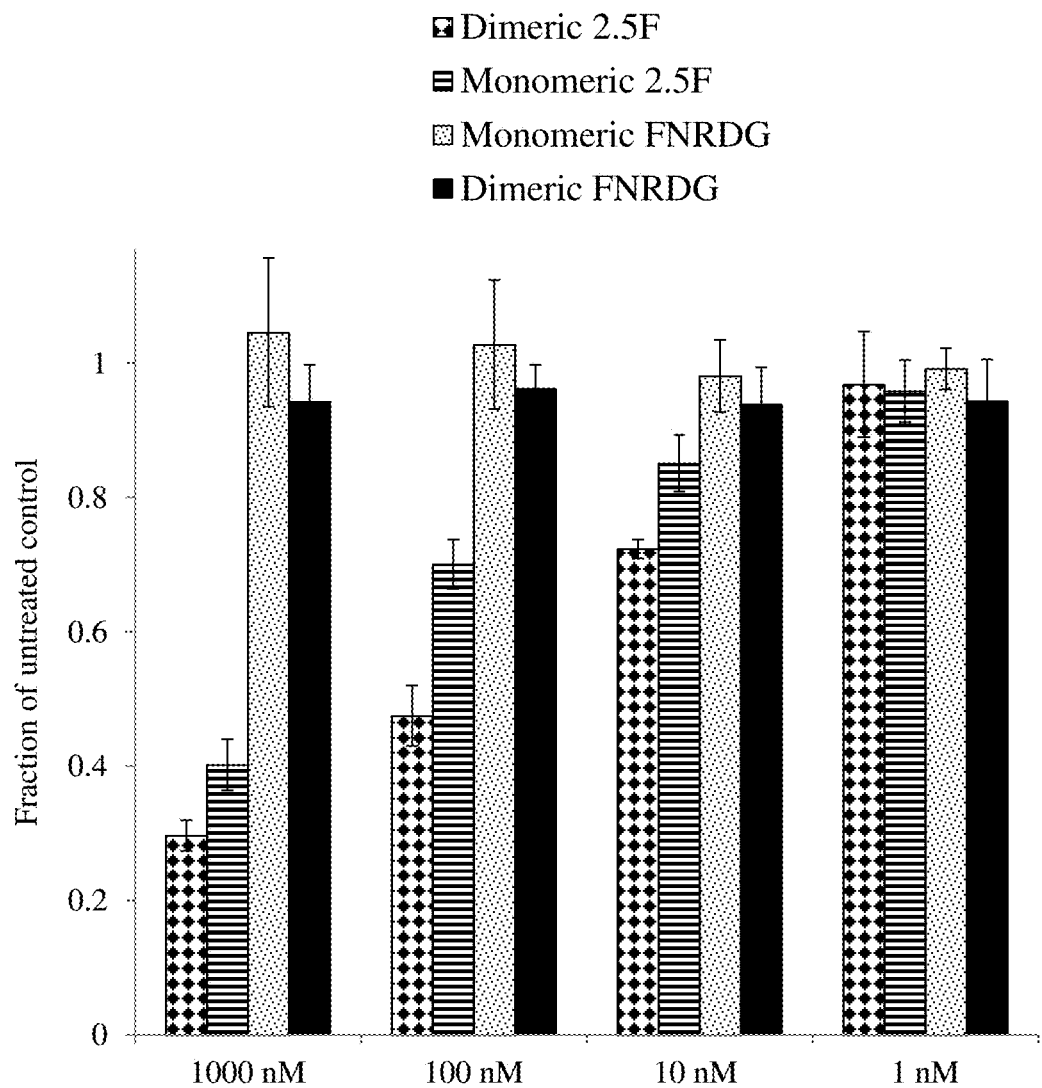
FIG. 4B is a bar graph showing dose dependent cytotoxicity of U87MG cells assessed by treating with different concentrations of knottins for 72 h and measuring cell viability using the AlamarBlue indicator dye.

Both EETI 2.5F monomer and dimer inhibited U87MG cell proliferation in time-dependent manner, with the dimer exhibiting significantly higher potency (FIG. 4A). At a concentration of 500 nM, EETI 2.5F dimer induced 53%, 68%, and 69% inhibition while EETI 2.5F monomer induced 37%, 44%, and 50% inhibition after 24, 48, and 72 h of treatment, respectively. Dose-dependent inhibition of U87MG proliferation was also observed (FIG. 4B). At concentrations of 1000 nM, 100 nM, and 10 nM after 72 hours of treatment, EETI 2.5F dimer induced 70%, 52%, and 28% inhibition, while the EETI 2.5F monomer induced 60%, 30%, and 15% inhibition, respectively. The scrambled EETI FNRDG monomer and dimer did not induce significant inhibition, demonstrating that the cytotoxicity was mediated by binding to the integrins.

Example 6: Conjugation of Drugs for Targeted Delivery

Figure 5:
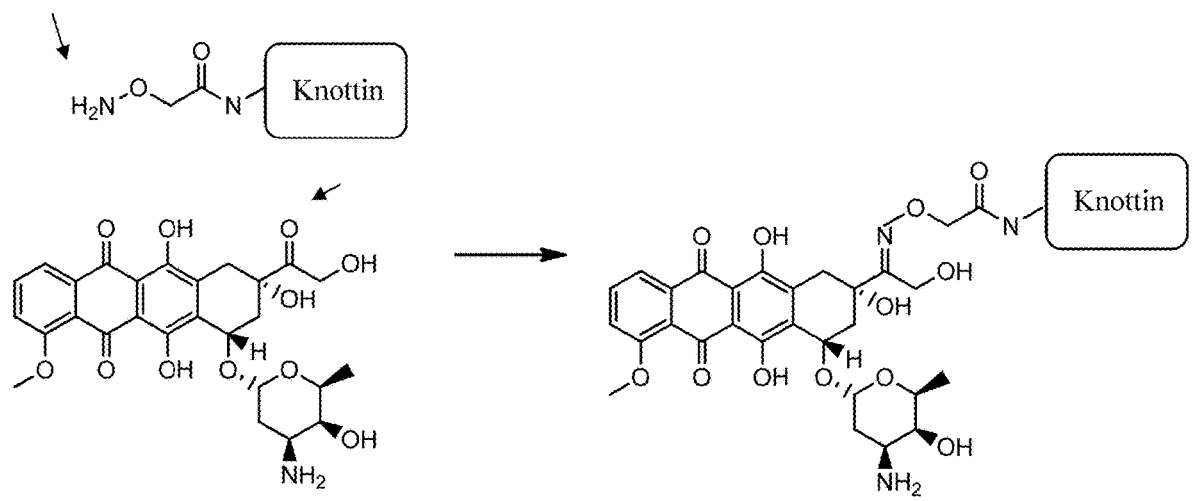
FIG. 5 is a drawing showing the general scheme for the conjugation of doxorubicin to the engineered knottin via an oxime bond.

In this example, a knottin containing an aminooxy residue is added to a mixture containing a therapeutic molecule, such as doxorubicin. Mixed with PBS at 25° C., the ketone group on the therapeutic molecule doxorubicin interacts with the aminooxy group of the non-natural amino acid on the knottin peptide, producing the conjugate (FIG. 5).

Conjugating a therapeutic small molecule to the knottin peptide provides an effective means for targeted drug delivery. Doxorubicin is used in cancer chemotherapy and interacts with DNA. Its ketone group can react with the aminooxy group of the knottin peptide monomer. Additionally, the knottins are able to traverse the vasculature, allowing delivery of the therapeutic agent to brain tumors.

EETI 2.5D and EETI 2.5F were conjugated with doxorubicin in this manner. The conjugate was purified using reverse phase HPLC with a 0.1% formic acid in acetonitrile gradient over 20 minutes. The conjugate elutes at 7.33 minutes (data not shown). The resulting purified conjugate was further verified using electrospray ionization-mass spectrosometry (ESI-MS).

Example 7: Exemplary Peptide Modifications

The above-exemplified knottin sequences may be varied to produce other knottins for multimerizatioin that have substantial identity to those disclosed. The knottin sequences of the present invention, as described above, have (i) a scaffold portion, (ii) a binding loop portion, and (iii) an aminooxy (AO) residue or other non-natural amino acid. The non-natural amino acid is advantageously placed adjacent to a binding loop; however, in certain embodiments it may be placed at a terminus. The AO was placed at the C-terminus of AgRP.

The scaffold portion provides the structural framework and is made rigid by disulfide binds between the cystine residues underlined in the exemplary sequence by the engineered EETI-11, 2.5F_AO:
$G_1\underline{C_2}P_3R_4P_5R_6G_7D_8N_9P_{10}P_{11}L_{12}T_{13}$
$\underline{C_{14}}X_{15}Q_{16}D_{17}S_{18}D_{19}C_{20}L_{21}A_{22}G_{23}C_{24}V_{25}C_{26}G_{27}P_{28}$
$N_{29}G_{30}G_{31}C_{32}G_{33}$ (SEQ ID NO: 3). One may introduce other residues in the scaffold portion of the peptide. The scaffold portion is residues G1, C2 and C14 to the carboxy end. The binding loop, as described above, is residues P3-C14. The underlined cysteine residues should be maintained in order to preserve the three dimensional structure. The remainder of the scaffold can be varied by conservative substitutions, e.g 2-3 amino acid substitutions. For example, in GCP-RPRGDNPPLT-CXQDSDCLAGCVCPNGFCG (SEQ ID NO: 3) wherein the italicized L21, A22, V25 and G30 residues may instead be another amino acid which is A, G, L, S, T, or V. Similarly, the binding loop may be modified with 1 amino acid substitution, 2 amino acid substitutions, or three amino acid substitutions. For example, R4 could be H or L. The binding core of RGD (residues 6-8) should not be varied.

As to the binding loop (bolded in SEQ ID NO: 3), the RGD sequence should be invariant, as stated previously. The other positions may be substituted as taught in Cochran et al. US 20090257952, "Engineered Integrin Binding Peptides," published Oct. 15, 2009. As stated there, the RGD-containing loop may be varied from the specific sequences disclosed. For example the loop sequence of EETI 2.5F, shown between P and C may be varied by 8 of the amino acids, but are invariant as to the RGD sequence. The other residues can be varied to a certain degree without affecting binding specificity and potency. For example, if three of the eleven residues were varied, one would have about 70% identity to 2.5F. For guidance in selecting which residues to vary, histograms in FIG. 11 (of the previously cited 20090257952) presents information on likely residues for each position. For example, in position −3 (the first X), one would most likely use a proline residue, based on isolated mutants that had positive integrin binding. However, His or Leu are also possible choices, as shown by their higher incidence in mutants with good integrin binding properties.

In specific, the present engineered knotttin peptides may be dimers that contain integrin binding portions, and the peptide comprising (i) a binding sequence specific to bind to at least one of αvβ5 integrin, αvβ3 integrin and α5β1 integrin, and (ii) a knottin protein scaffold, said binding sequence being comprised in said knottin protein scaffold and being an 11 amino acid engineered integrin binding loop, 11 amino acids long comprising the sequence RGD, wherein said RGD is in the sequence between residues 3 and 7 in an 11 residue binding loop; (iii), and said knottin protein scaffold, except for the engineered integrin binding loop, being substantially identical to one of: EETI-II, AgRP, mini-AGRP, agatoxin or miniagatoxin, wherein, when the knottin protein scaffold is substantially identical to EETI-II, said integrin binding peptide has a sequence at least 90% identical having three or fewer amino acid substitutions to a peptide.

The present peptides contain at least one non-natural amino acid, in particular an amino acid residue with a side chain comprising an aminooxy, —N—C(=O)—CH2-O—NH2.

The present knottin may contain a binding loop portion between the 11 residues loop, said binding loop being within a scaffold portion, wherein said scaffold portion may have up to two amino acid substitutions so as to be at least 90% identical to SEQ ID NO: 3, SEQ NO: 5. Residue P1s in the binding loop above, (See SEQ NO: 2) can be selected from the group consisting of A, V, L, P, F, Y, S, H, D, and N; $R_2$ is selected from the group consisting of G, V, L, P, R, E, and Q; $P_3$ is selected from the group consisting of G, A, and P; $N_7$ is selected from the group consisting of W and N; $P_8$ is selected from the group consisting of A, P, and S; $P_9$ is selected from the group consisting of P and R; $L_{10}$ is selected from the group consisting of A, V, L, P, S, T, and E; and $T_{11}$ is selected from the group consisting of G, A, W, S, T, K, and E.

Variants and AgRp Mini Peptide (SEQ ID NO: 8)
GCVRLHESCLGQQVPCCDPAATCYCY₁G₂RGDN₆D₇L₈R₉CYCX may be made, for example as follows, with respect to the binding loop (bolded above):
$Y_1$ may be F, W or H
$G_2$ may be A, S or V
$N_6$ may be D, Y
$D_7$ may be N or Y
$L_8$ may be I, V, or F, and
$R_9$ may be K or N. The aminooxy (AO) residue is as illustrated above. In this embodiment, the AO non-natural amino acid is positioned at the carboxy terminus of the peptide.

As to the scaffold portion of the peptide (un-bolded) two to three amino acids may be substituted. This is shown for the following examples:

(SEQ ID NO: 9)
GCVRLHE S→V CLGQQVPCCDPAATCYCY₁G₂RGDN₆D₇L₈R₉CYCX, (SEQ ID NO: 11)
GCVRLHESCLGQQVPCCDPA A→G TCYCY₁G₂RGDN₆D₇L₈R₉CYCX, (SEQ ID NO: 12)
GCVRLHESCLGQQVPCC D→E PAATCYCY₁G₂RGDN₆D₇L₈R₉CYCX, and so forth.

Variations of EETI-II

As further examples, one may vary the location of the non-natural amino acid. EETI-II 2.5F_AO has the AO (shown as "X") in place of the lysine at position 15: GC PRPRGDNPPLTCXQDSDCLAGCVCGPNGFCG (SEQ ID NO: 3). In other words, As before, the binding loop is bolded. EETI 2.5F_AO may be shown by residue number as follows:

(SEQ ID NO: 3)
$G_1C_2P_3R_4P_5R_6G_7D_8N_9P_{10}P_{11}L_{12}T_{13}C_{14}X_{15}Q_{16}D_{17}S_{18}D_{19}C_{20}L_{21}A_{22}G_{23}C_{24}$
$V_{25}C_{26}G_{27}P_{28}N_{29}G_{30}F_{31}C_{32}G_{33}$.

EETI 2.5F_AO-2 is GCPRPRGDNPPLTCQDSD-CLAGCVCGPNGFCGX (SEQ ID NO: 13). This exemplified addition of the AO (shown as "X") to the carboxyl terminal end, i.e. following residue 33.

Using the above numbering, one may see that the AO residue or other non-natural amino acid may be used, for example in place of any one of residues AO15-G23, residues G27-F31, or other loops. Another variant was constructed, based on EETI 2.5D, which binds αvβ3 and αvβ5 integrin:

EETI 2.5D
(SEQ ID NO: 4)
GCPQGRGDWAPTSCKQDSDCRAGCVCGPNGFCG

EETI 2.5D_AO
(SEQ ID NO: 5)
GCPQGRGDWAPTSCXQDSDCRAGCVCGPNGFCG,

X=AO.

EETI 2.5D_AO has the same numbering as the EETI2.5F_AO, although the sequence is different; the AO residue is at position 15, as in EETI 2.5F-AO. Variations in sequences may be made as described in connection with sequence EETI 2.5F.

Example 8: Comparison of EETI 2.5F Knottin Monomer and Dimer to Cilengitide

As is known, Cilengitide is a molecule designed and synthesized at the Technical University Munich in collaboration with Merck KGaA in Darmstadt. It is based on the cyclic peptide cyclo(-RGDfV-), which is selective for αv integrins, which are important in angiogenesis (forming new blood vessels). Hence, it is under investigation for the treatment of glioblastoma by inhibiting angiogenesis. The European Medicines Agency has granted cilengitide orphan drug status.

Figure 6:
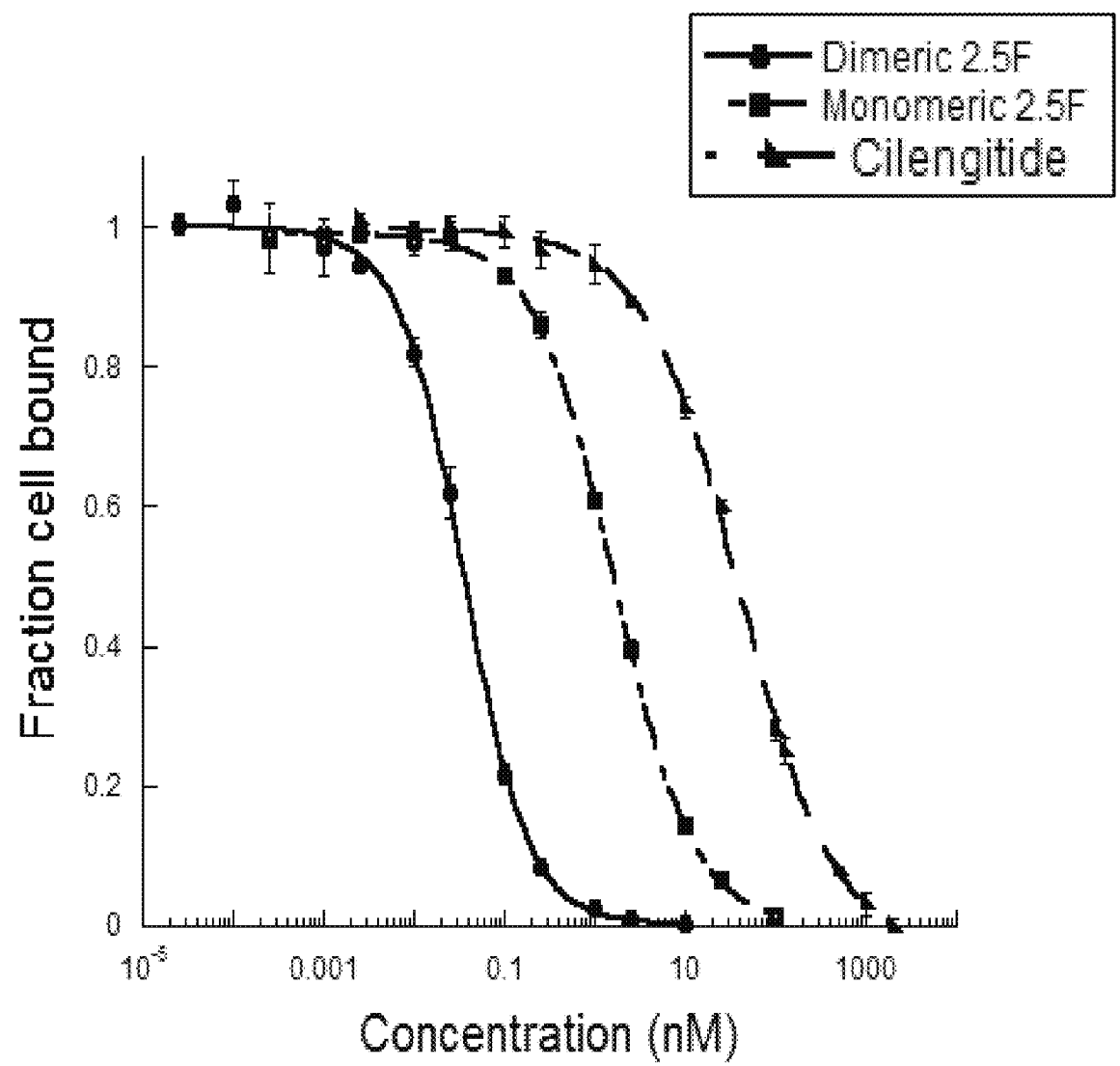
FIG. 6 is a graph showing a competition assay of EETI-based integrin binding proteins dimeric 2.5F and monomeric 2.5F to U87MG cells compared to Cilengitide, as measured by flow cytometry. Alexa488-labeled EETI 2.5F was used as a competitor.
Figure 7:
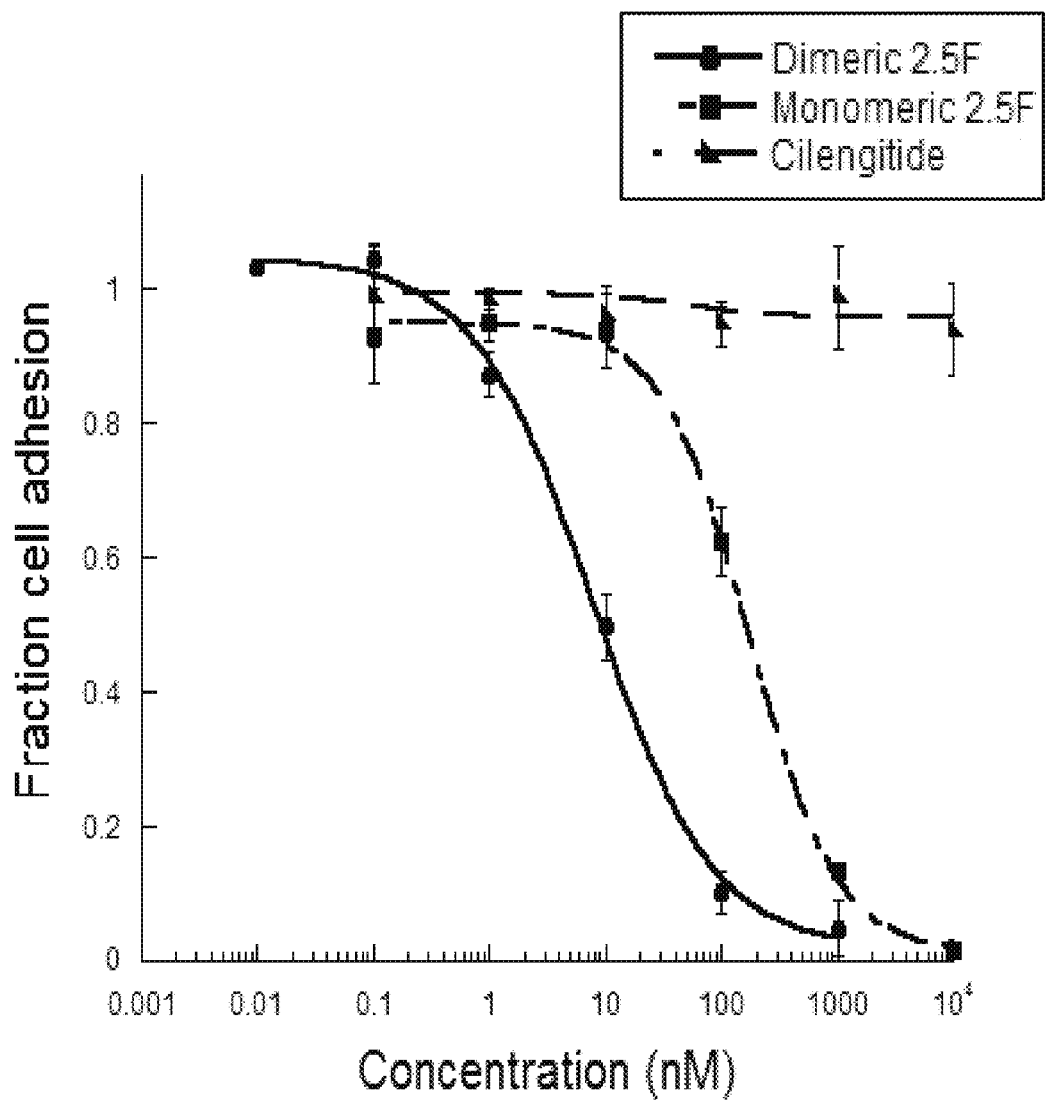
FIG. 7 is a graph measuring comparative inhibition of adhesion of U87MG cells treated with dimeric and monomeric 2.5F or Cilgenitide to fibronectin, a component of ECM. Fibronectin coated plates were incubated with U87MG cells with the indicated concentrations of peptides. Adherent cells remaining after several wash steps were quantified with crystal violet staining by absorbance at 600 nm. Values were normalized to negative control containing no competing peptides.
Figure 8:
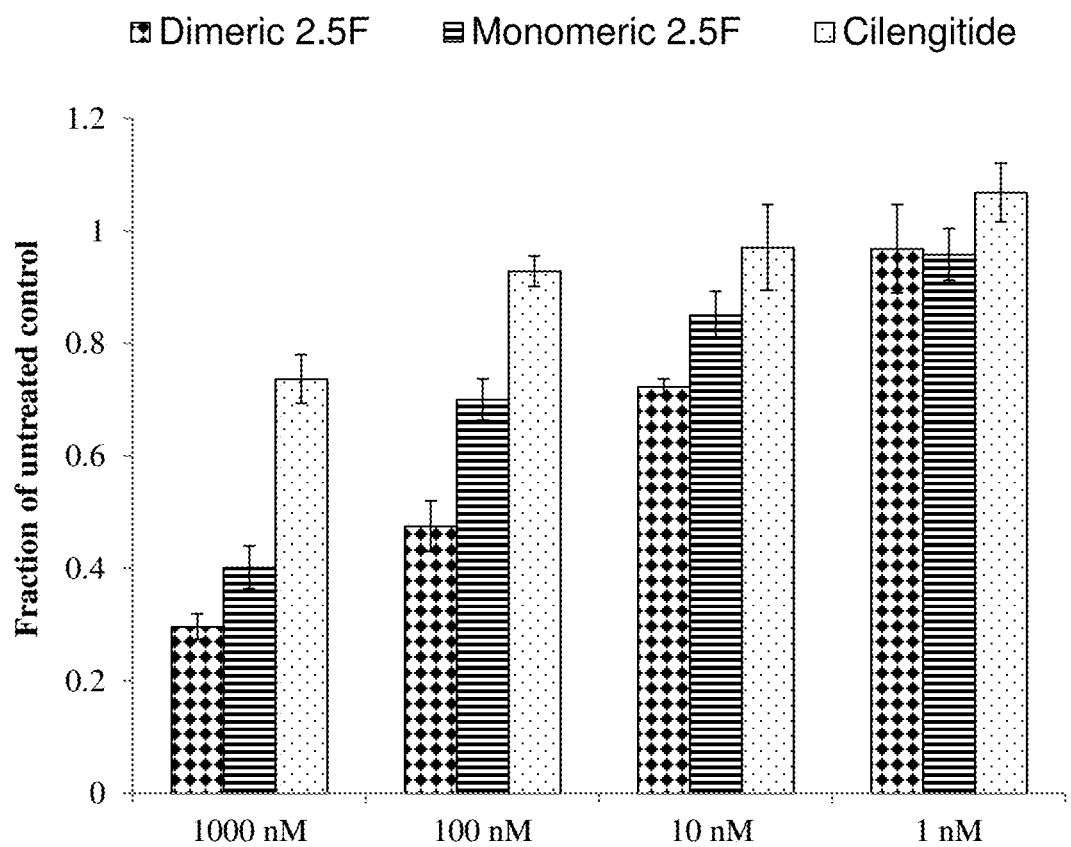
FIG. 8 is a bar graph showing dose dependent cytotoxicity of U87MG cells assessed by treating with different concentrations of dimeric or monomeric 2.5F or Cilgenitide for 72 h and measuring cell viability using the AlamarBlue indicator dye.

Relative U87MG binding affinity, and inhibition of U87MG cell adhesion and proliferation was measured for the EETI 2.5F dimer, EETI 2.5F monomer, and Cilengitide as described in Examples 3, 4, and 5. The relative binding affinity ($IC_{50}$) of Cilengitide to U87MG cells (using 0.25 nM of Alexa488-labeled EETI 2.5F as the competitor) was 41±2 nM compared to 1.64±0.03 nM for the EETI 2.5F monomer and 0.036±0.002 nM for the EETI 2.5F dimer (FIG. 6). Unlike the EETI 2.5F dimer and EETI 2.5F monomer, Cilengitide does not inhibit U87MG cell adhesion to fibronectin at the highest concentration tested (FIG. 7). Remarkably, the EETI 2.5F dimer is 100-fold more potent at inhibiting cell proliferation compared to Cilengitide (FIG. 8).

Example 9: Pharmaceutical Compositions

The present engineered knottins may be used for imaging or for therapeutic purposes, as demonstrated above. The present peptides may also be formulated as pharmaceutical compositions for use in vivo in humans. Suitable formulations may be derived by reference to U.S. Pat. No. 7,262,165, entitled "Aqueous preparation containing oligopeptides and etherified cyclodextrin," issued Aug. 28, 2007. Briefly, as described there, the knottin to be used will be soluble in water or a suitable buffer such as physiological saline. Based on this solubility, a concentration of knottin peptide in the solution of the pharmaceutical composition may be determined. For example, if the peptide has a saturation solubility in physiological saline solution of about 19 mg/ml and it can therefore, for therapeutic use, be safely administered parenterally in a concentration of 15 mg/ml dissolved in physiological saline solution. If, for example, a dose of 1500 mg is necessary for therapy with the peptide, a volume to be administered of 100 ml arises. Volumes in this order of magnitude can no longer simply be injected and must be infused, which is disadvantageous. Pharmaceutically acceptable ingredients may be added to increase solubility or tolerance for injection. The present peptides may also be formulated in enteric form (see e.g. U.S. Pat. No. 5,350,741). Other formulations which may be employed are in Remington: The Science and Practice of Pharmacy, 19th Edition (1995) and/or Handbook of pharmaceutical granulation technology, chapter 7, "Drugs and the pharmaceutical sciences", vol. 81, 1997. In further embodiments of the present compositions, carriers are selected from hydrophilic binders, water-soluble diluents, surfactants, detergents, lubricants, disintegrants, antioxidants, non water-soluble diluents and/or other fillers known to the skilled person. In a particular embodiment the one or more carriers comprises at least a hydrophilic binder and a water-soluble diluent. Lyophilzed formulations may be prepared as described in U.S. Pat. No. 7,265,092, "Pharmaceutical compositions," issued Sep. 4, 2007, to Li. as described there, various excipients and anti-aggregants may be used.

Parenteral administration is generally characterized by injection, either subcutaneously, intramuscularly, intraperitoneal, intravenously, and in the case of the present invention via intra-tumor injection. Injectables can be prepared in conventional forms, either as liquid solutions or suspensions, solid (e.g., dried or lyophilized) forms suitable for reconstitution into solution or suspension in liquid prior to injection, or as emulsions. Generally, suitable excipients include, for example, water, saline, dextrose, glycerol, ethanol or the like. In addition, minor amounts of non-toxic auxiliary substances can be employed, such as wetting or emulsifying agents, pH buffering agents, solubility enhancers, tonicifiers and the like including, for example, sodium acetate, sorbitan monolaurate, triethanolamine oleate, cyclodextrins, etc. Dosage forms for intravenous (IV) administration generally comprise an active peptide agent incorporated into a sterile solution of simple chemicals such as sugars, amino acids or electrolytes, which can be easily carried by the circulatory system and assimilated. Such solutions are typically prepared with saline or buffer. The pH of such IV fluids may vary, and will typically be from 3.5 to 8.0, as known in the art.

Example 10: Cell Inhibition of Proliferation with Dimer Knottins

Dimers of the present knottins with AO groups incorporated at different positions were prepared and conjugated with different linkages. There were tested for activity against carcinoma lines. Results are shown below in Table 3. As identified there, Dimer 1 is EETI 2.5F where the AO group was incorporated in place of Lys15, conjugated through the 17.3 Angstrom linker shown in FIG. 1B; Dimer 2 is EETI 2.5F, where the AO group was incorporated in place of Lys15, conjugated though the 68.5 Angstrom linker shown in FIG. 9. Dimer 3 is EETI 2.5F, where the AO group was incorporated at the C-terminus following residue 33, conjugated through a 17.3 Angstrom linker shown in FIG. 1B; Dimer 4 is EETI 2.5F, where the AO group was incorporated at the C-terminus following residue 33, conjugated through the 68.5 Angstrom linker shown in FIG. 9. It was observed that the position of the AO residue had a strong effect on binding activity. Peptide dimers with AO at position at 15 exhibited stronger binding than peptides with AO at the C-terminus. Also, it was observed that the length of the linkage had only a minor effect on binding. Binding, of course, it correlated with the activity in proliferation and apoptosis.

TABLE 3

|  | Proliferation | Apoptosis (Caspase-3) |
|---|---|---|
| Cell line: MDA231 (Human breast adenocarcinoma) | | |
| Cilengitide | Weak inhibition | Moderate induction |
| 2.5F Monomer | Weak inhibition | Moderate induction |
| 2.5F Dimer1 | Strong inhibition | Strong induction |
| 2.5F Dimer2 | Strong inhibition | N/A |
| 2.5F Dimer3 | Moderate inhibition | N/A |
| 2.5F Dimer4 | Moderate inhibition | N/A |
| Cell line: SKOV 3 (Ovarian adenocarcinoma) | | |
| Cilengitide | N/A | N/A |
| 2.5F Monomer | N/A | N/A |
| 2.5F Dimer1 | Strong inhibition | N/A |
| 2.5F Dimer2 | Strong inhibition | N/A |
| 2.5F Dimer3 | N/A | N/A |
| 2.5F Dimer4 | N/A | N/A |

The results above indicate that EETI 2.5F Dimers 1 and 2 more strongly inhibited tumor cell proliferation compared to Dimers 3 and 4, demonstrating that the location of the AO group within the knottin mattered (position 15 versus C-terminus), but the crosslinker length did not (17.3 versus 68.5 angstroms). All dimers, however, were more potent at inhibiting tumor cell proliferation compared to EETI 2.5F monomer and Cilengitide.

Example 11: Additional Linkages

As described above, the present dimers are constructed of two engineered knottin peptides (e.g. EET-II and AgRP), where the peptides contain a binding loop, and, in the scaffold portion, at least one non-natural amino residue. The non-natural amino residue has a side chain that can bond to a linkage molecule. By example, the non-natural amino acid contains an aminooxy functional group. The linker molecule contains functional groups in their terminal portions. Each linker molecule can bond to two different engineered peptides. For example, the linker molecules are terminated with aldehyde groups. Alternative, the linker molecules can carry more than two functional groups, to form multimers of 3, 4, 5, or more, engineered knottins.

Figure 9:
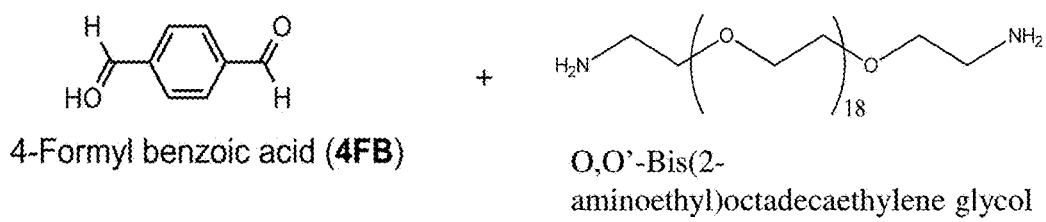
FIG. 9 is a drawing showing the chemical structure for 4-formyl benzoic acid (4FB) as shown in FIG. 1A, which was reacted with a different starting material to generate a longer cross-linker.
Figure 9:
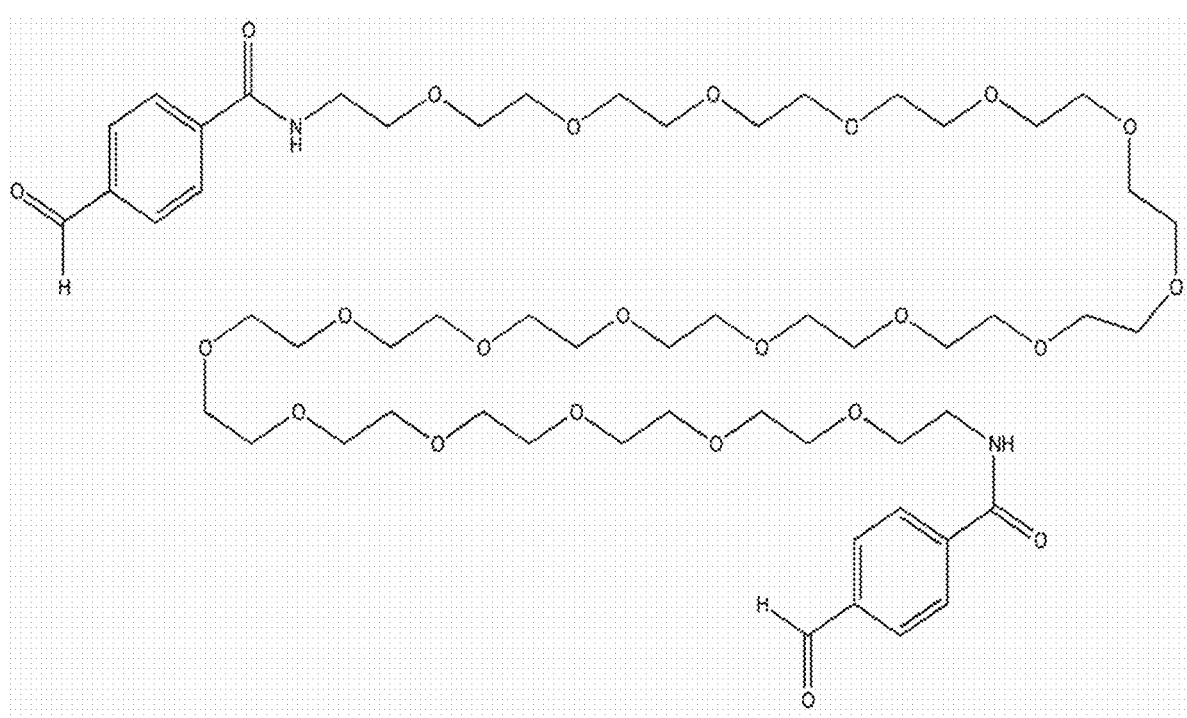

FIG. 9 illustrates linkage molecules having terminal aldehyde groups (4-formylbenzamide) and an alkoxy chain linking the aldehyde-bearing groups. In the compound in FIG. 9, O,O'-Bis(2-aminoethyl)octadecaethylene glycol was reacted with 4-Formyl benzoic acid (4FB) (similarly to the method of Example 2) to generate the crosslinker: N,N'-(3,6,9,12,15,18,21,24,27,30,33,36,39,42,45,48,51,54,57-nonadecaoxanonapentacontane-1,59-diyl)bis(4-formylbenzamide). As can be appreciated, the various ethylene glycol monomers can be varied; instead of 18, one could use 2, as in FIG. 1, or any number in between. One could use more than 18, e.g. as between 18 and 40 ethylene glycol monomers.

CONCLUSION

The above specific description is meant to exemplify and illustrate the invention and should not be seen as limiting the scope of the invention, which is defined by the literal and equivalent scope of the appended claims. Any patents or publications mentioned in this specification, including the below cited references are indicative of levels of those skilled in the art to which the patent pertains and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the methods and materials.

REFERENCES

1. Mbeunkui, F.; Johann, D. J., Jr. *Cancer Chemother Pharmacol* 2009, 63, 571.
2. Grassian, A. R.; Coloff, J. L.; Brugge, J. S. *Cold Spring Harb Symp Quant Biol* 2011, 76, 313.
3. Tredan, O.; Galmarini, C. M.; Patel, K.; Tannock, I. F. *J Natl Cancer Inst* 2007, 99, 1441.
4. Miranti, C. K.; Brugge, J. S. *Nat Cell Biol* 2002, 4, E83.
5. Desgrosellier, J. S.; Cheresh, D. A. *Nat Rev Cancer* 2010, 10, 9.
6. Brooks, P. C.; Clark, R. A.; Cheresh, D. A. *Science* 1994, 264, 569.
7. Kim, S.; Bell, K.; Mousa, S. A.; Varner, J. A. *Am J Pathol* 2000, 156, 1345.
8. Mizejewski, G. J. *Proc Soc Exp Biol Med* 1999, 222, 124.
9. Stupack, D. G.; Cheresh, D. A. *Curr Top Dev Biol* 2004, 64, 207.
10. Haas, T. A.; Plow, E. F. *Curr Opin Cell Biol* 1994, 6, 656.
11. Kimura, R. H.; Levin, A. M.; Cochran, F. V.; Cochran, J. R. *Proteins* 2009, 77, 359.
12. Silverman, A. P.; Levin, A. M.; Lahti, J. L.; Cochran, J. R. *J Mol Biol* 2009, 385, 1064.
13. Pallaghy, P. K.; Nielsen, K. J.; Craik, D. J.; Norton, R. S. *Protein Sci* 1994, 3, 1833.
14. Werle, M.; Schmitz, T.; Huang, H. L.; Wentzel, A.; Kolmar, H.; Bernkop-Schnurch, A. *J Drug Target* 2006, 14, 137.
15. Chiche, L.; Heitz, A.; Gelly, J. C.; Gracy, J.; Chau, P. T.; Ha, P. T.; Hernandez, J. F.; Le-Nguyen, D. *Curr Protein Pept Sci* 2004, 5, 341.
16. Craik, D. J.; Daly, N. L.; Waine, C. *Toxicon* 2001, 39, 43.
17. Mecca, T.; Consoli, G. M. L.; Geraci, C.; Cunsolo, F. *Bioorgan Med Chem* 2004, 12, 5057.
18. Jain, R. K.; Hamilton, A. D. *Org Lett* 2000, 2, 1721.
19. Kitov, P. I.; Lipinski, T.; Paszkiewicz, E.; Solomon, D.; Sadowska, J. M.; Grant, G. A.; Mulvey, G. L.; Kitova, E. N.; Klassen, J. S.; Armstrong, G. D.; Bundle, D. R. *Angew Chem Int Edit* 2008, 47, 672.

20. Garanger, E.; Boturyn, D.; Coll, J. L.; Favrot, M. C.; Dumy, P. *Org Biomol Chem* 2006, 4, 1958.
21. Kok, R. J.; Schraa, A. J.; Bos, E. J.; Moorlag, H. E.; Asgeirsdottir, S. A.; Everts, M.; Meijer, D. K.; Molema, G. *Bioconjug Chem* 2002, 13, 128.
22. Hersel, U.; Dahmen, C.; Kessler, H. *Biomaterials* 2003, 24, 4385.
23. Hu, B.; Finsinger, D.; Peter, K.; Guttenberg, Z.; Barmann, M.; Kessler, H.; Escherich, A.; Moroder, L.; Bohm, J.; Baumeister, W.; Sui, S. F.; Sackmann, E. *Biochemistry* 2000, 39, 12284.
24. Thumshirn, G.; Hersel, U.; Goodman, S. L.; Kessler, H. *Chemistry* 2003, 9, 2717.
25. Kantlehner, M.; Finsinger, D.; Meyer, J.; Schaffner, P.; Jonczyk, A.; Diefenbach, B.; Nies, B.; Kessler, H. *Angew Chem Int Edit* 1999, 38, 560.
26. Oliveira-Ferrer, L.; Hauschild, J.; Fiedler, W.; Bokemeyer, C.; Nippgen, J.; Celik, I.; Schuch, G. *J Exp Clin Canc Res* 2008, 27.
27. Rose, K. *J Am Chem Soc* 1994, 116, 30.
28. Shao, J.; Tam, J. P. *J Am Chem Soc* 1995, 117, 3893.
29. Canne, L. E.; Ferredamare, A. R.; Burley, S. K.; Kent, S. B. H. *J Am Chem Soc* 1995, 117, 2998.
30. Krause, S.; Schmoldt, H. U.; Wentzel, A.; Ballmaier, M.; Friedrich, K.; Kolmar, H. *Febs J* 2007, 274, 86.
31. Aguzzi, M. S.; Giampietri, C.; De Marchis, F.; Padula, F.; Gaeta, R.; Ragone, G.; Capogrossi, M. C.; Facchiano, A. *Blood* 2004, 103, 4180.
32. Abdollahi, A.; Griggs, D. W.; Zieher, H.; Roth, A.; Lipson, K. E.; Saffrich, R.; Grone, H. J.; Hallahan, D. E.; Reisfeld, R. A.; Debus, J.; Niethammerl, A. G.; Huber, P. E. *Clinical Cancer Research* 2005, 11, 6270.
33. Buckley, C. D.; Pilling, D.; Henriquez, N. V.; Parsonage, G.; Threlfall, K.; Scheel-Toellner, D.; Simmons, D. L.; Albar, A. N.; Lord, J. M.; Salmon, M. *Nature* 1999, 397, 534.

What is claimed is:

1. A method of making a knottin-drug conjugate, comprising:
   conjugating a small molecule drug to a knottin peptide, wherein the knottin peptide comprises a non-natural amino acid comprising a functional group selected from the group consisting of: aldehyde, ketone, alkyne, alkene, aryl halide, diene, azide, and aminooxy,
   wherein the conjugating comprises conjugating the small molecule drug to the non-natural amino acid via a linker molecule.

2. The method according to claim 1, wherein the knottin peptide comprises an *Ecballium elaterium* trypsin inhibitor (EETI) scaffold portion.

3. The method according to claim 2, wherein the knottin peptide comprises an engineered binding loop portion.

4. The method according to claim 3, wherein the engineered binding loop portion comprises an RGD sequence.

5. The method according to claim 4, wherein the knottin peptide comprises an amino acid sequence that is at least 80% identical to SEQ ID NO:2 or SEQ ID NO:4.

6. The method according to claim 4, wherein the knottin peptide comprises the amino acid sequence set forth in SEQ ID NO:2 or SEQ ID NO:4.

7. The method according to claim 1, wherein the knottin peptide comprises an Agouti-related protein (AgRP) scaffold portion.

8. The method according to claim 7, wherein the knottin peptide comprises an engineered binding loop portion.

9. The method according to claim 8, wherein the engineered binding loop portion comprises an RGD sequence.

10. The method according to claim 9, wherein the knottin peptide comprises an amino acid sequence that is at least 80% identical to SEQ ID NO:7.

11. The method according to claim 9, wherein the knottin peptide comprises the amino acid sequence set forth in SEQ ID NO:7.

12. The method according to claim 1, wherein the knottin peptide comprises a non-natural amino acid comprising an azide functional group.

13. The method according to claim 12, wherein the conjugating comprises Huisgen cycloaddition.

14. The method according to claim 1, wherein the linker comprises a polymeric chain.

15. The method according to claim 14, wherein the polymeric chain comprises ethylene glycol monomers.

16. The method according to claim 1, wherein the linker comprises a polymeric chain selected from the group consisting of: polyethylene glycol, polyether, alkyl, polypeptide, β-peptide, and polypeptoid.

17. The method according to claim 1, wherein the small molecule drug is a small molecule anti-cancer drug.

18. The method according to claim 17, wherein the small molecule anti-cancer drug is an anthracycline-based small molecule anti-cancer drug.

19. The method according to claim 18, wherein the anthracycline-based small molecule anti-cancer drug is doxorubicin.

20. The method according to claim 3, wherein the non-natural amino acid is adjacent to the engineered binding loop or at the carboxyl-terminus of the knottin peptide.

* * * * *